US008187850B2

(12) United States Patent
Rybak et al.

(10) Patent No.: US 8,187,850 B2
(45) Date of Patent: May 29, 2012

(54) METHOD FOR PRODUCING AN L-AMINO ACID USING A BACTERIUM OF THE ENTEROBACTERIACEAE FAMILY WITH ATTENUATED EXPRESSION OF THE *YBIV* GENE

(75) Inventors: Konstantin Vyacheslavovich Rybak, Moscow (RU); Marina Evgenievna Sheremet'eva, Moscow (RU); Aleksandra Yurievna Skorokhodova, Moscow (RU); Tatyana Viktorovna Leonova, Moscow (RU); Yury Ivanovich Kozlov, Moscow (RU); Vitaly Grigorievich Paraskevov, legal representative, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 992 days.

(21) Appl. No.: 12/022,299

(22) Filed: Jan. 30, 2008

(65) Prior Publication Data
US 2010/0279362 A1 Nov. 4, 2010

Related U.S. Application Data

(63) Continuation of application No. PCT/JP2006/315993, filed on Aug. 8, 2006.

(60) Provisional application No. 60/743,258, filed on Feb. 9, 2006.

(30) Foreign Application Priority Data

Aug. 9, 2005 (RU) ................................ 2005125292

(51) Int. Cl.
*C12P 1/04* (2006.01)
(52) U.S. Cl. ........ 435/170; 435/106; 435/107; 435/108; 435/109; 435/110; 435/113; 435/114; 435/115; 435/116; 435/252.1; 435/252.8
(58) Field of Classification Search ........................ None
See application file for complete search history.

(56) References Cited

U.S. PATENT DOCUMENTS

| | | | |
|---|---|---|---|
| 6,960,455 B2 | 11/2005 | Livshits et al. | |
| 7,138,266 B2 | 11/2006 | Debabov et al. | |
| 7,179,623 B2 | 2/2007 | Livshits et al. | |
| 7,186,531 B2 | 3/2007 | Akhverdian et al. | |
| 7,300,786 B2 | 11/2007 | Klyachko et al. | |
| 2004/0132165 A1 | 7/2004 | Akhverdian et al. | |
| 2004/0229320 A1 | 11/2004 | Stoynova et al. | |
| 2005/0048631 A1 | 3/2005 | Klyachko et al. | |
| 2005/0176033 A1 | 8/2005 | Klyachko et al. | |
| 2005/0191684 A1* | 9/2005 | Zimenkov et al. ................. 435/6 |
| 2005/0214911 A1 | 9/2005 | Marchenko et al. | |
| 2005/0239175 A1 | 10/2005 | Tabolina et al. | |
| 2006/0014257 A1 | 1/2006 | Katashkina et al. | |
| 2006/0035346 A1 | 2/2006 | Savrasova et al. | |
| 2006/0035348 A1 | 2/2006 | Gulevich et al. | |
| 2006/0040365 A1 | 2/2006 | Kozlov et al. | |
| 2006/0063240 A1 | 3/2006 | Katashkina et al. | |
| 2006/0088919 A1 | 4/2006 | Rybak et al. | |
| 2006/0141586 A1 | 6/2006 | Rybak et al. | |
| 2006/0160192 A1 | 7/2006 | Rybak et al. | |
| 2006/0286643 A1 | 12/2006 | Sheremet'eva et al. | |
| 2007/0184532 A1 | 8/2007 | Klyachko et al. | |
| 2007/0212764 A1 | 9/2007 | Ptitsyn et al. | |

FOREIGN PATENT DOCUMENTS

WO WO03/014370 A2 2/2003

OTHER PUBLICATIONS

Imaizumi et al., Journal of Biotechnology, Apr. 2005, vol. 117, p. 111-118.*
Roberts et al., Proteins, 2005, vol. 58, p. 790-801.*
Mori, H., English translation of Bioscience & Industry, vol. 562, p. 167, 2004, pp. 1-9.*
Bongaerts et al., Metabolic Engineering, 2001, vol. 3, p. 289-300.*
International Preliminary Report on Patentability and Written Opinion of the International Searching Authority for PCT Patent App. No. PCT/JP2006/315993 (Feb. 21, 2008).
Roberts, A., et al., "YbiV From *Escherichia coli* K12 is a HAD Phosphatase," Proteins: Structure, Function, and Bioinformatics 2005;58:790-801.
International Search Report and Written Opinion of the International Searching Authority for PCT Patent App. No. PCT/JP2006/315993 (Dec. 12, 2006).
U.S. Appl. No. 60/586,222, filed Jul. 9, 2004, Akhverdian et al.
U.S. Appl. No. 60/587,492, filed Jul. 14, 2004, Klyachko et al.
U.S. Appl. No. 60/604,698, filed Aug. 27, 2004, Zimenkov et al.
U.S. Appl. No. 60/610,545, filed Sep. 17, 2004, Marchenko et al.
U.S. Appl. No. 60/644,562, filed Jan. 19, 2005, Rybak et al.
U.S. Appl. No. 60/673,807, filed Apr. 22, 2005, Rybak et al.
U.S. Appl. No. 60/693,507, filed Jun. 24, 2005, Rybak et al.
U.S. Appl. No. 60/693,509, filed Jun. 24, 2005, Sheremet'eva et al.
U.S. Appl. No. 60/703,414, filed Jul. 29, 2005, Ptitsyn et al.
U.S. Appl. No. 60/703,426, filed Jul. 29, 2005, Rybak et al.
U.S. Appl. No. 60/703,444, filed Jul. 29, 2005, Rybak et al.
U.S. Appl. No. 60/714,843, filed Sep. 8, 2005, Filippov et al.
U.S. Appl. No. 60/714,850, filed Sep. 8, 2005, Gulevich et al.
U.S. Appl. No. 60/723,566, filed Oct. 5, 2005, Rybak et al.
U.S. Appl. No. 60/723,924, filed Oct. 6, 2005, Rybak et al.
U.S. Appl. No. 60/723,925, filed Oct. 6, 2005, Rybak et al. U.S. Appl. No. 60/723,928, filed Oct. 6, 2005, Rybak et al.
U.S. Appl. No. 60/743,222, filed Feb. 3, 2006, Rybak et al.
U.S. Appl. No. 60/743,223, filed Feb. 3, 2006, Rybak et al.
U.S. Appl. No. 60/743,226, filed Feb. 3, 2006, Rybak et al.
U.S. Appl. No. 60/743,257, filed Feb. 9, 2006, Rybak et al.
U.S. Appl. No. 60/743,258, filed Feb. 9, 2006, Rybak et al.
U.S. Appl. No. 60/806,819, filed Jul. 10, 2006, Rybak et al.
U.S. Appl. No. 60/807,258, filed Jul. 20, 2006, Filippov et al.
U.S. Appl. No. 60/826,820, filed Sep. 25, 2006, Kotliarova et al.
U.S. Appl. No. 11/536,863, filed Sep. 29, 2006, Zakataeva et al.
U.S. Appl. No. 60/829,697, filed Oct. 17, 2006, Rybak et al.
U.S. Appl. No. 60/829,706, filed Oct. 17, 2006, Filippov et al.

(Continued)

*Primary Examiner* — Kade Ariani
(74) *Attorney, Agent, or Firm* — Shelly Guest Cermak; Cermack Nakajima LLP

(57) ABSTRACT

The present invention provides a method for producing an L-amino acid using a bacterium of the Enterobacteriaceae family, particularly a bacterium belonging to genus *Escherichia* or *Pantoea*, which has been modified to attenuate expression of the ybiV gene.

7 Claims, 3 Drawing Sheets

OTHER PUBLICATIONS

U.S. Appl. No. 60/829,923, filed Oct. 18, 2006, Filippov et al.
U.S. Appl. No. 60/829,926, filed Oct. 18, 2006, Rybak et al.
U.S. Appl. No. 60/867,151, filed Nov. 24, 2006, Rybak et al.
U.S. Appl. No. 60/885,671, filed Jan. 19, 2007, Ptitsyn et al.
U.S. Appl. No. 60/894,996, filed Mar. 15, 2007, Rybak et al.
U.S. Appl. No. 11/830,961, filed Jul. 31, 2007, Filippov et al.
U.S. Appl. No. 11/830,969, filed Jul. 31, 2007, Gulevich et al.
U.S. Appl. No. 11/830,974, filed Jul. 31, 2007, Filippov et al.
U.S. Appl. No. 11/849,403, filed Sep. 4, 2007, Rybak et al.
U.S. Appl. No. 11/952,297, filed Dec. 7, 2007, Rybak et al.
U.S. Appl. No. 12/173,379, filed Jan. 22, 2008, Rybak et al.

\* cited by examiner

METHOD FOR PRODUCING AN L-AMINO ACID USING A BACTERIUM OF THE ENTEROBACTERIACEAE FAMILY WITH ATTENUATED EXPRESSION OF THE YBIV GENE

The present application claims priority under 35 U.S.C. §119 to Russian Patent Application No. 2005125292, filed Aug. 9, 2005, and U.S. Provisional Patent Application No. 60/743,258, filed Feb. 9, 2006, and is a continuation under 35 U.S.C. §120 to PCT Patent Application No. PCT/JP2006/315993, filed Aug. 8, 2006, the entireties of which are incorporated by reference. Also, the Sequence Listing filed electronically via EFS-Web herewith is hereby incorporated by reference (File name: US-241_Seq_List_Copy__1; File size: 15 KB; Date recorded: Jan. 30, 2008).

BACKGROUND OF THE INVENTION

1. Field of the Invention

The present invention relates to the microbiological industry, and specifically to a method for producing an L-amino acid using a bacterium of the Enterobacteriaceae family which has been modified to attenuate expression of the ybiV gene.

2. Brief Description of the Related Art

The ybiV gene in *Escherichia coli* encodes the YbiV protein, a hypothetical protein with sequence homology to the haloacid dehalogenase (HAD) superfamily of proteins. Although numerous members of this family have been identified, the functions of few are known. Using the crystal structure, sequence analysis, and biochemical assays, YbiV has been characterized as a HAD phosphatase. The crystal structure of YbiV reveals a two-domain protein, one domain with the characteristic HAD hydrolase fold, and the other domain with an inserted alpha/beta fold. In order to understand the mechanism, the structure of YbiV complexed with beryllofluoride ($BeF_3^-$) and aluminum trifluoride ($AlF_3$) has been determined. This structure mimics the phosphorylated intermediate and transition state for hydrolysis, respectively, similar to other HAD phosphatases. Analysis of the structures reveals the substrate-binding cavity, which is hydrophilic in nature. Both structure and sequence homology indicate that YbiV may be a sugar phosphatase, and this indication is supported by biochemical assays that measured the release of free phosphate on a number of sugar-like substrates (Roberts, A. et al. YbiV from *Escherichia coli* K12 is a HAD phosphatase. Proteins, 2005, 58(4):790-801).

But currently, there have been no reports of inactivating the ybiV gene for the purpose of producing L-amino acids.

SUMMARY OF THE INVENTION

Aspects of the present invention include enhancing the productivity of L-amino acid-producing strains and providing a method for producing an L-amino acid using these strains.

The above aspects were achieved by finding that attenuating expression of the ybiV gene can enhance production of L-amino acids, such as L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, L-arginine, L-phenylalanine, L-tyrosine, and L-tryptophan.

The present invention provides a bacterium of the Enterobacteriaceae family having an increased ability to produce amino acids, such as L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, L-arginine, L-phenylalanine, L-tyrosine, and L-tryptophan.

It is an aspect of the present invention to provide an L-amino acid-producing bacterium of the Enterobacteriaceae family, wherein the bacterium has been modified to attenuate expression of the ybiV gene.

It is a further aspect of the present invention to provide the bacterium as described above, wherein the expression of the ybiV gene is attenuated by inactivation of the ybiV gene.

It is a further aspect of the present invention to provide the bacterium as described above, wherein the bacterium belongs to the genus *Escherichia*.

It is a further aspect of the present invention to provide the bacterium as described above, wherein the bacterium belongs to the genus *Pantoea*.

It is a further aspect of the present invention to provide the bacterium as described above, wherein said L-amino acid is selected from the group consisting of an aromatic L-amino acid and a non-aromatic L-amino acid.

It is a further aspect of the present invention to provide the bacterium as described above, wherein said aromatic L-amino acid is selected from the group consisting of L-phenylalanine, L-tyrosine, and L-tryptophan.

It is a further aspect of the present invention to provide the bacterium as described above, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine.

It is a further aspect of the present invention to provide a method for producing an L-amino acid comprising:
cultivating the bacterium as described above in a medium to produce and excrete said L-amino acid into the medium, and
collecting said L-amino acid from the medium.

It is a further aspect of the present invention to provide the method as described above, wherein said L-amino acid is selected from the group consisting of an aromatic L-amino acid and a non-aromatic L-amino acid.

It is a further aspect of the present invention to provide the method as described above, wherein said aromatic L-amino acid is selected from the group consisting of L-phenylalanine, L-tyrosine, and L-tryptophan.

It is a further aspect of the present invention to provide the method as described above, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine.

The present invention is described in detail below.

DESCRIPTION OF THE PREFERRED EMBODIMENTS

1. Bacterium of the Present Invention

Figure 1:
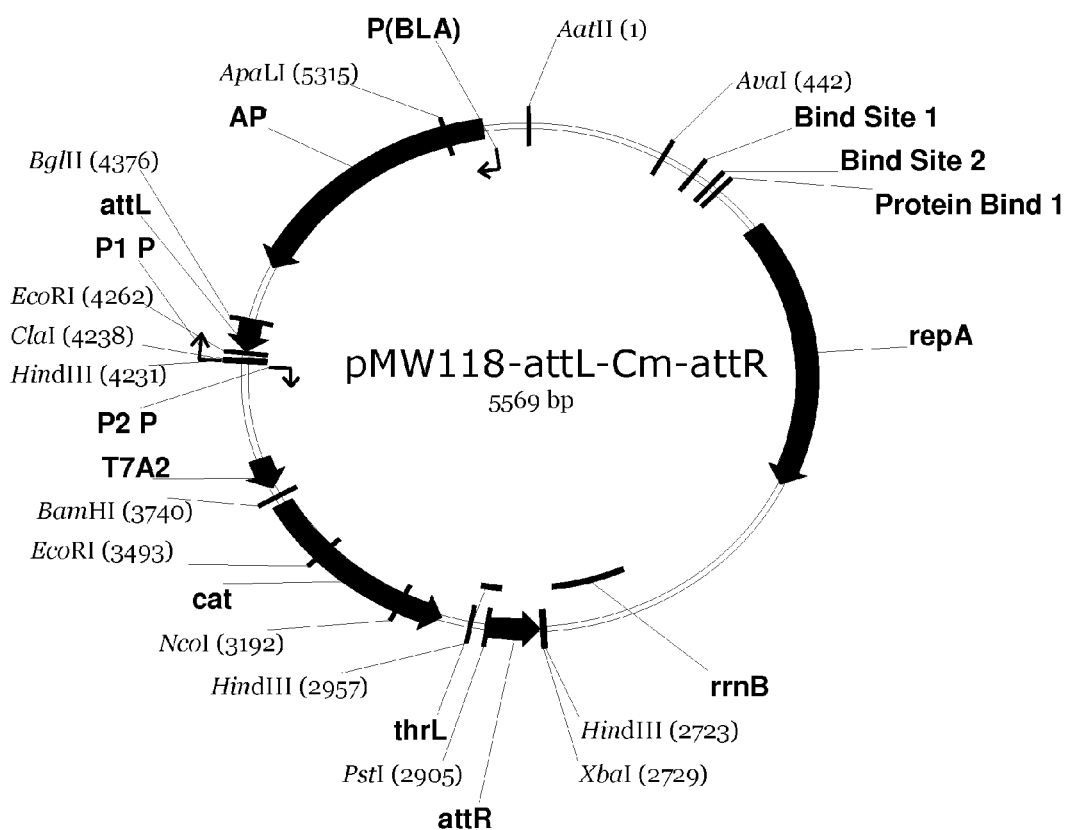
FIG. 1 shows the construction of the pMW118-attL-Cm-attR plasmid, which is used as a template for PCR.

The bacterium of the present invention is an L-amino acid-producing bacterium of the Enterobacteriaceae family, wherein the bacterium has been modified to attenuate expression of the ybiV gene.

In the present invention, "L-amino acid-producing bacterium" means a bacterium which is able to produce and excrete an L-amino acid into a medium, when the bacterium is cultured in the medium.

The term "L-amino acid-producing bacterium" as used herein also means a bacterium which is able to produce and cause accumulation of an L-amino acid in a culture medium in an amount larger than a wild-type or parental strain of the bacterium, for example, *E. coli*, such as *E. coli* K-12, and preferably means that the bacterium is able to cause accumulation in a medium of an amount not less than 0.5 g/L, more preferably not less than 1.0 g/L, of the target L-amino acid. The term "L-amino acid" includes L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, and L-valine.

The term "aromatic L-amino acid" includes L-phenylalanine, L-tyrosine, and L-tryptophan. The term "non-aromatic L-amino acid" includes L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine. L-threonine, L-lysine, L-cysteine, L-leucine, L-histidine, L-glutamic acid, L-phenylalanine, L-tryptophan, L-proline and L-arginine are particularly preferred.

The Enterobacteriaceae family includes bacteria belonging to the genera *Escherichia*, *Enterobacter*, *Erwinia*, *Klebsiella*, *Pantoea*, *Photorhabdus*, *Providencia*, *Salmonella*, *Serratia*, *Shigella*, *Morganella Yersinia*, etc. Specifically, those classified into the Enterobacteriaceae according to the taxonomy used by the NCBI (National Center for Biotechnology Information) database (http://www.ncbi.nlm.nih.gov/Taxonomy/Browser/wwwtax.cgi?id=91347) can be used. A bacterium belonging to the genus *Escherichia* or *Pantoea* is preferred.

The phrase "a bacterium belonging to the genus *Escherichia*" means that the bacterium is classified into the genus *Escherichia* according to the classification known to a person skilled in the art of microbiology. Examples of a bacterium belonging to the genus *Escherichia* as used in the present invention include, but are not limited to, *Escherichia coli* (*E. coli*).

The bacterium belonging to the genus *Escherichia* that can be used in the present invention is not particularly limited; however, e.g., bacteria described by Neidhardt, F. C. et al. (*Escherichia coli* and *Salmonella typhimurium*, American Society for Microbiology, Washington D.C., 1208, Table 1) are encompassed by the present invention.

The phrase "a bacterium belonging to the genus *Pantoea*" means that the bacterium is classified into the genus *Pantoea* according to the classification known to a person skilled in the art of microbiology. Some species of *Enterobacter agglomerans* have been recently re-classified into *Pantoea agglomerans*, *Pantoea ananatis*, *Pantoea stewartii* or the like, based on the nucleotide sequence analysis of 16S rRNA, etc. (Int. J. Syst. Bacteriol., 43, 162-173 (1993)).

The phrase "bacterium has been modified to attenuate expression of the ybiV gene" means that the bacterium has been modified in such a way that the modified bacterium contains a reduced amount of the YbiV protein, as compared with an unmodified bacterium, or the modified bacterium is unable to synthesize the YbiV protein. The phrase "bacterium has been modified to attenuate expression of the ybiV gene" also means that the target gene is modified in such a way that the modified gene encodes a mutant YbiV protein which has a decreased activity.

The phrase "inactivation of the ybiV gene" means that the modified gene encodes a completely non-functional protein. It is also possible that the modified DNA region is unable to naturally express the gene due to the deletion of a part of the gene, the shifting of the reading frame of the gene, the introduction of missense/nonsense mutation(s), or the modification of an adjacent region of the gene, including sequences controlling gene expression, such as a promoter, enhancer, attenuator, ribosome-binding site, etc.

The ybiV gene encodes the YbiV protein, an HAD phosphatase (synonym—b0822). The ybiV gene of *E. coli* (nucleotide positions 859,251 to 858,436; GenBank accession no. NC_000913.2; gi:49175990; SEQ ID NO: 1) is located between the ybiU and ybiW genes on the chromosome of *E. coli* K-12. The nucleotide sequence of the ybiV gene and the amino acid sequence of YbiV encoded by the ybiV gene are shown in SEQ ID NO: 1 and SEQ ID NO: 2, respectively.

Since there may be some differences in DNA sequences between the genera or strains of the Enterobacteriaceae family, the ybiV gene to be inactivated on the chromosome is not limited to the gene shown in SEQ ID No: 1, but may include genes homologous to SEQ ID No: 1 encoding a variant of the YbiV protein. The phrase "variant protein" as used in the present invention means a protein which has changes in the sequence, whether they are deletions, insertions, additions, or substitutions of amino acids, but still maintains the activity of the product as the YbiV protein. The number of changes in the variant protein depends on the position or the type of amino acid residues in the three dimensional structure of the protein. It may be 1 to 30, preferably 1 to 15, and more preferably 1 to 5 in SEQ ID NO: 2. These changes in the variants can occur in regions of the protein which are not critical for the function of the protein. This is because some amino acids have high homology to one another so the three dimensional structure or activity is not affected by such a change. These changes in the variant protein can occur in regions of the protein which are not critical for the function of the protein. Therefore, the protein variant encoded by the ybiV gene may have a homology of not less than 80%, preferably not less than 90%, and most preferably not less than 95%, with respect to the entire amino acid sequence shown in SEQ ID NO. 2, as long as the ability of the YbiV protein as a transcription regulator prior to inactivation is maintained.

Homology between two amino acid sequences can be determined using the well-known methods, for example, the computer program BLAST 2.0, which calculates three parameters: score, identity and similarity.

Moreover, the ybiV gene may be a variant which hybridizes under stringent conditions with the nucleotide sequence shown in SEQ ID NO: 1, or a probe which can be prepared from the nucleotide sequence, provided that it encodes a functional YbiV protein prior to inactivation. "Stringent conditions" include those under which a specific hybrid, for example, a hybrid having homology of not less than 60%, preferably not less than 70%, more preferably not less than 80%, still more preferably not less than 90%, and most preferably not less than 95%, is formed and a non-specific hybrid, for example, a hybrid having homology lower than the above, is not formed. For example, stringent conditions are exemplified by washing one time or more, preferably two or three times, at a salt concentration of 1×SSC, 0.1% SDS, preferably 0.1×SSC, 0.1% SDS at 60° C. Duration of washing depends on the type of membrane used for blotting and, as a rule, may be what is recommended by the manufacturer. For example, the recommended duration of washing for the Hybond™ N+ nylon membrane (Amersham) under stringent conditions is 15 minutes. Preferably, washing may be performed 2 to 3 times. The length of the probe may be suitably selected, depending on the hybridization conditions, and usually varies from 100 bp to 1 kbp.

Expression of the ybiV gene can be attenuated by introducing a mutation into the gene on the chromosome so that intracellular activity of the protein encoded by the gene is decreased as compared with an unmodified strain. Such a mutation on the gene can be replacement of one base or more to cause amino acid substitution in the protein encoded by the gene (missense mutation), introduction of a stop codon (nonsense mutation), deletion of one or two bases to cause a frame shift, insertion of a drug-resistance gene, or deletion of a part of the gene or the entire gene (Qiu, Z. and Goodman, M. F., J. Biol. Chem., 272, 8611-8617 (1997); Kwon, D. H. et al, J. Antimicrob. Chemother., 46, 793-796 (2000)). Expression of the ybiV gene can also be attenuated by modifying an expression regulating sequence such as the promoter, the Shine-Dalgarno (SD) sequence, etc. (WO95/34672, Carrier, T. A. and Keasling, J. D., Biotechnol Prog 15, 58-64 (1999)).

For example, the following methods may be employed to introduce a mutation by gene recombination. A mutant gene encoding a mutant protein having a decreased activity is prepared, and the bacterium to be modified is transformed with a DNA fragment containing the mutant gene. Then, the native gene on the chromosome is replaced with the mutant gene by homologous recombination, and the resulting strain is selected. Such gene replacement using homologous recombination can be conducted by employing a linear DNA, which is known as "Red-driven integration" (Datsenko, K. A. and Wanner, B. L., Proc. Natl. Acad. Sci. USA, 97, 12, p 6640-6645 (2000)), or by employing a plasmid containing a temperature-sensitive replication origin (U.S. Pat. No. 6,303,383 or JP 05-007491A). Furthermore, the incorporation of a site-specific mutation by gene substitution using homologous recombination such as set forth above can also be conducted with a plasmid lacking the ability to replicate in the host When a marker gene such as antibiotic resistant gene is used to prepare the mutant gene or to detect recombination between the mutant gene and the native gene on the chromosome, the marker gene can be eliminated from the chromosome by, for example, a method described in the Examples section.

Expression of the gene can also be attenuated by insertion of a transposon or an IS factor into the coding region of the gene (U.S. Pat. No. 5,175,107), or by conventional methods, such as mutagenesis using UV irradiation or nitrosoguanidine (N-methyl-N'-nitro-N-nitrosoguanidine) treatment.

The presence of activity of the YbiV protein can be detected by complementation of mutation ybiV by the method described, for example, in Roberts, A. et al. YbiV from *Escherichia coli* K12 is a HAD phosphatase. Proteins, 2005, 58(4):790-801. Thus, the reduced or absent activity of the YbiV protein in the bacterium can be determined when compared to the parent unmodified bacterium.

The presence or absence of the ybiV gene on the chromosome of a bacterium can be detected by well-known methods, including PCR, Southern blotting and the like. In addition, the level of gene expression can be estimated by measuring the amount of mRNA transcribed from the gene using various well-known methods, including Northern blotting, quantitative RT-PCR, and the like. The amount or molecular weight of the protein encoded by the gene can be measured by well-known methods, including SDS-PAGE followed by immunoblotting assay (Western blotting analysis) and the like.

Methods for preparation of plasmid DNA, digestion and ligation of DNA, transformation, selection of an oligonucleotide as a primer, and the like may be ordinary methods well-known to one skilled in the art. These methods are described, for instance, in Sambrook, J., Fritsch, E. F., and Maniatis, T., "Molecular Cloning: A Laboratory Manual, Second Edition", Cold Spring Harbor Laboratory Press (1989).

L-Amino Acid-Producing Bacteria

As a bacterium of the present invention which is modified to attenuate expression of the ybiV gene, bacteria which are able to produce either an aromatic or a non-aromatic L-amino acid may be used.

The bacterium of the present invention can be obtained by attenuating expression of the ybiV gene in a bacterium which inherently has the ability to produce an L-amino acid. Alternatively, the bacterium of present invention can be obtained by imparting the ability to produce an L-amino acid to a bacterium already having attenuated expression of the ybiV gene.

L-Threonine-Producing Bacteria

Examples of parent strains for deriving the L-threonine-producing bacteria of the present invention include, but are not limited to, strains belonging to the genus *Escherichia*, such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A), and the like.

The strain TDH-6 is deficient in the thrC gene, as well as being sucrose-assimilative, and the ilvA gene has a leaky mutation. This strain also has a mutation in the rhtA gene, which imparts resistance to high concentrations of threonine or homoserine. The strain B-3996 contains the plasmid pVIC40 which was obtained by inserting a thrA*BC operon which includes a mutant thrA gene into a RSF1010-derived vector. This mutant thrA gene encodes aspartokinase homoserine dehydrogenase I which is substantially desensitized to feedback inhibition by threonine. The strain B-3996 was deposited on Nov. 19, 1987 in the All-Union Scientific Center of Antibiotics (Nagatinskaya Street 3-A, 117105 Moscow, Russian Federation) under the accession number RIA 1867. The strain was also deposited in the Russian National Collection of Industrial Microorganisms (VKPM) (Russia, 117545 Moscow, 1 Dorozhny proezd. 1) on Apr. 7, 1987 under the accession number VKPM B-3996.

*E. coli* VKPM B-5318 (EP 0593792B) may also be used as a parent strain for deriving L-threonine-producing bacteria of the present invention. The strain B-5318 is prototrophic with regard to isoleucine, and a temperature-sensitive lambda-phage C1 repressor and PR promoter replaces the regulatory region of the threonine operon in plasmid pVIC40. The strain VKPM B-5318 was deposited in the Russian National Collection of Industrial Microorganisms (VKPM) on May 3, 1990 under accession number of VKPM B-5318.

Preferably, the bacterium of the present invention is additionally modified to enhance expression of one or more of the following genes:

the mutant thrA gene which codes for aspartokinase homoserine dehydrogenase I resistant to feed back inhibition by threonine;
the thrB gene which codes for homoserine kinase;
the thrC gene which codes for threonine synthase;
the rhtA gene which codes for a putative transmembrane protein;
the asd gene which codes for aspartate-β-semialdehyde dehydrogenase; and
the aspC gene which codes for aspartate aminotransferase (aspartate transaminase);

The thrA gene which encodes aspartokinase homoserine dehydrogenase I of *Escherichia coli* has been elucidated (nucleotide positions 337 to 2799, GenBank accession NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide positions 2801 to 3733, GenBank accession NC_000913.2, gi: 49175990). The thrB gene is located between the thrA and thrC genes on the chromosome of *E. coli* K-12. The thrC gene which encodes threonine synthase of *Escherichia coli* has been elucidated (nucleotide positions 3734 to 5020, GenBank accession NC_000913.2, gi: 49175990). The thrC gene is located between the thrB gene and the yaaX open reading frame on the chromosome of *E. coli* K-12. All three genes functions as a single threonine operon. To enhance expression of the threonine operon, the attenuator region which affects the transcription is desirably removed from the operon (WO2005/049808, WO2003/097839).

A mutant thrA gene which codes for aspartokinase homoserine dehydrogenase I resistant to feed back inhibition by threonine, as well as the thrB and thrC genes, can be obtained as one operon from well-known plasmid pVIC40 which is present in the threonine producing *E. coli* strain VKPM B-3996. Plasmid pVIC40 is described in detail in U.S. Pat. No. 5,705,371.

The rhtA gene exists at 18 min on the *E. coli* chromosome close to the glnHPQ operon, which encodes components of the glutamine transport system. The rhtA gene is identical to ORF1 (ybiF gene, nucleotide positions 764 to 1651, GenBank accession number AAA218541, gi:440181) and located between the pexB and ompX genes. The unit expressing a protein encoded by the ORF1 has been designated the rhtA gene (rht: resistance to homoserine and threonine). Also, it was revealed that the rhtA23 mutation is an A-for-G substitution at position-1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The asd gene of *E. coli* has already been elucidated (nucleotide positions 3572511 to 3571408, GenBank accession NC_000913.1, gi:16131307), and can be obtained by PCR (polymerase chain reaction; refer to White, T. J. et al., Trends Genet., 5, 185 (1989)) utilizing primers prepared based on the nucleotide sequence of the gene. The asd genes of other microorganisms can be obtained in a similar manner.

Also, the aspC gene of *E. coli* has already been elucidated (nucleotide positions 983742 to 984932, GenBank accession NC_000913.1, gi:16128895), and can be obtained by PCR. The aspC genes of other microorganisms can be obtained in a similar manner.

L-Lysine-Producing Bacteria

Examples of L-lysine-producing bacteria belonging to the genus *Escherichia* include mutants having resistance to an L-lysine analogue. The L-lysine analogue inhibits growth of bacteria belonging to the genus *Escherichia*, but this inhibition is fully or partially desensitized when L-lysine is present in the culture medium. Examples of the L-lysine analogue include, but are not limited to, oxalysine, lysine hydroxamate, S-(2-aminoethyl)-L-cysteine (AEC), γ-methyllysine, α-chlorocaprolactam and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The strain WC196 may be used as an L-lysine producing bacterium of *Escherichia coli*. This bacterial strain was bred by conferring AEC resistance to the strain W3110, which was derived from *Escherichia coli* K-12. The resulting strain was designated *Escherichia coli* AJ13069 and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of parent strains for deriving L-lysine-producing bacteria of the present invention also include strains in which expression of one or more genes encoding an L-lysine biosynthetic enzyme are enhanced. Examples of such genes include, but are not limited to, genes encoding dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyruvate carboxylase (ppc), aspartate semialdehyde dehydrogenase (asd), and aspartase (aspA) (EP 1253195 A). In addition, the parent strains may have an increased level of expression of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), or combinations thereof.

Examples of parent strains for deriving L-lysine-producing bacteria of the present invention also include strains having decreased or eliminated activity of an enzyme that catalyzes a reaction generating a compound other than L-lysine by branching off from the biosynthetic pathway of L-lysine. Examples of these enzymes include homoserine dehydrogenase, lysine decarboxylase (U.S. Pat. No. 5,827,698), and the malic enzyme (WO2005/010175).

L-Cysteine-Producing Bacteria

Examples of parent strains for deriving L-cysteine-producing bacteria of the present invention include, but are not limited to, strains belonging to the genus *Escherichia*, such as *E. coli* JM15 which is transformed with different cysE alleles coding for feedback-resistant serine acetyltransferases (U.S. Pat. No. 6,218,168, Russian patent application 2003121601); *E. coli* W3110 over-expressing genes which encode proteins suitable for secreting substances toxic for cells (U.S. Pat. No. 5,972,663); *E. coli* strains with lowered cysteine desulfohydrase activity (JP11155571A2); *E. coli* W3110 with increased activity of a positive transcriptional regulator for the cysteine regulon encoded by the cysB gene (WO0127307A1), and the like.

L-Leucine-Producing Bacteria

Examples of parent strains for deriving L-leucine-producing bacteria of the present invention include, but are not limited to, strains belonging to the genus *Escherichia*, such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5,5-trifluoroleucine (JP 62-34397 B and JP 8-70879 A); *E. coli* strains obtained by the gene engineering method described in WO96/06926; *E. coli* H-9068 (JP 8-70879 A), and the like.

The bacterium of the present invention may be improved by enhancing the expression of one or more genes involved in L-leucine biosynthesis. Examples include genes of the leuABCD operon, which are preferably represented by a mutant leuA gene coding for isopropylmalate synthase not subject to feedback inhibition by L-leucine (U.S. Pat. No. 6,403,342). In addition, the bacterium of the present invention may be improved by enhancing the expression of one or more genes coding for proteins which excrete L-amino acid from the bacterial cell. Examples of such genes include the b2682 and b2683 genes (ygaZH genes) (EP 1239041 A2).

L-Histidine-Producing Bacteria

Examples of parent strains for deriving L-histidine-producing bacteria of the present invention include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP1085087); *E. coli* AI80/pFM201 (U.S. Pat. No. 6,258,554) and the like.

Examples of parent strains for deriving L-histidine-producing bacteria of the present invention also include strains in which expression of one or more genes encoding an L-histidine biosynthetic enzyme is enhanced. Examples of such genes include genes encoding ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that L-histidine biosynthetic enzymes encoded by hisG and hisBHAFI are inhibited by L-histidine, and therefore an L-histidine-producing ability can also be efficiently enhanced by introducing a mutation conferring resistance to the feedback inhibition into ATP phosphoribosyltransferase Russian Patent Nos. 2003677 and 2119536).

Specific examples of strains having an L-histidine-producing ability include *E. coli* FERM-P 5038 and 5048 which have been introduced with a vector carrying a DNA encoding an L-histidine-biosynthetic enzyme (JP 56-005099 A), *E. coli* strains transformed with rht, a gene for amino acid-export (EP1016710A), *E. coli* 80 strain imparted with sulfaguanidine, DL-1,2,4-triazole-3-alanine, and streptomycin-resistance (VKPM B-7270, Russian Patent No. 2119536), and so forth.

L-Glutamic Acid-Producing Bacteria

Examples of parent strains for deriving L-glutamic acid-producing bacteria of the present invention include, but are not limited to, strains belonging to the genus *Escherichia*, such as *E. coli* VL334thrC$^+$ (EP 1172433). *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 grown on the wild-type *E. coli* strain K12 (VKPM B-7) cells. As a result, an L-isoleucine auxotrophic strain VL334thrC$^+$ (VKPM B-8961), which is able to produce L-glutamic acid, was obtained.

Examples of parent strains for deriving the L-glutamic acid-producing bacteria of the present invention include, but are not limited to, strains in which expression of one or more genes encoding an L-glutamic acid biosynthetic enzyme is enhanced. Examples of such genes include genes encoding glutamate dehydrogenase (gdh), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate dehydrogenase (aceEF, aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), and glucose phosphate isomerase (pgi).

Examples of strains modified so that expression of the citrate synthetase gene, the phosphoenolpyruvate carboxylase gene, and/or the glutamate dehydrogenase gene is/are enhanced include those disclosed in EP1078989A, EP955368A, and EP952221A.

Examples of parent strains for deriving the L-glutamic acid-producing bacteria of the present invention also include strains having decreased or eliminated activity of an enzyme that catalyzes synthesis of a compound other than L-glutamic acid by branching off from an L-glutamic acid biosynthesis pathway. Examples of such genes include genes encoding isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), and glutamate decarboxylase (gadAB). Bacteria belonging to the genus *Escherichia* deficient in α-ketoglutarate dehydrogenase activity or having a reduced α-ketoglutarate dehydrogenase activity and methods for obtaining them are described in U.S. Pat. Nos. 5,378,616 and 5,573,945. Specifically, these strains include the following:

*E. coli*W3110sucA::Kmr
*E. coli* AJ12624 (FERM BP-3853)
*E. coli* AJ12628 (FERM BP-3854)
*E. coli* AJ12949 (FERM BP-4881)

*E. coli* W3110sucA::Kmr is obtained by disrupting the α-ketoglutarate dehydrogenase gene (hereinafter referred to as "sucA gene") of *E. coli* W3110. This strain is completely deficient in α-ketoglutarate dehydrogenase.

Other examples of L-glutamic acid-producing bacterium include those which belong to the genus *Escherichia* and have resistance to an aspartic acid antimetabolite. These strains can also be deficient in α-ketoglutarate dehydrogenase activity and include, for example, *E. coli* AJ13199 (FERM BP-5807) (U.S. Pat. No. 5,908,768), FFRM P-12379, which additionally has a reduced ability to decompose L-glutamic acid (U.S. Pat. No. 5,393,671); AJ13138 (FERM BP-5565) (U.S. Pat. No. 6,110,714), and the like.

Examples of L-glutamic acid-producing bacteria, include mutant strains belonging to the genus *Pantoea* which are deficient in α-ketoglutarate dehydrogenase activity or have a decreased α-ketoglutarate dehydrogenase activity, and can be obtained as described above. Such strains include *Pantoea* ananatis AJ13356. (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645. It was then converted to an international deposit under the provisions of Budapest Treaty on Jan. 11, 1999 and received an accession number of FERM BP-6615. *Pantoea ananatis* AJ13356 is deficient in α-ketoglutarate dehydrogenase activity as a result of disruption of the αKGDH-E1 subunit gene (sucA). The above strain was identified as *Enterobacter agglomerans* when it was isolated and deposited as *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, it is described as *Pantoea ananatis*.

L-Phenylalanine-Producing Bacteria

Examples of parent strains for deriving L-phenylalanine-producing bacteria of the present invention include, but are not limited to, strains belonging to the genus *Escherichia*, such as *E. coli* AJ12739 (tyrA::Tn10, tyrR) (VKPM B-8197); *E. coli* HW1089 (ATCC 55371) harboring the mutant pheA34 gene (U.S. Pat. No. 5,354,672); *E. coli* MWEC101-b (KR8903681); *E. coli* NRRL B-12141, NRRL B-12145, NRRL B-12146 and NRRL B-12147 (U.S. Pat. No. 4,407,952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ 12604 (FERM BP-3579) may be used (EP 488-424 B1). Furthermore, L-phenylalanine producing bacteria belonging to the genus *Escherichia* with an enhanced activity of the protein encoded by the yedA gene or the yddG gene may also be used (U.S. patent applications 2003/0148473 A1 and 2003/0157667 A1).

L-Tryptophan-Producing Bacteria

Examples of parent strains for deriving the L-tryptophan-producing bacteria of the present invention include, but are not limited to, strains belonging to the genus *Escherichia*, such as *E. coli* JP4735/pMU3028 (DSM10122) and JP6015/pMU91 (DSM10123) which is deficient in the tryptophanyl-tRNA synthetase encoded by mutant trpS gene (U.S. Pat. No. 5,756,345); *E. coli* SV164 (pGH5) having a serA allele encoding phosphoglycerate dehydrogenase not subject to feedback inhibition by serine and a trpE allele encoding anthranilate synthase not subject to feedback inhibition by tryptophan (U.S. Pat. No. 6,180,373); *E. coli* AGX17 (pGX44) (NRRL B-12263) and AGX6(pGX50)aroP (NRRL B-12264) which is deficient in the enzyme tryptophanase (U.S. Pat. No. 4,371,614); *E. coli* AGX17/pGX50, pACKG4-pps in which a phosphoenolpyruvate-producing ability is enhanced (WO9708333, U.S. Pat. No. 6,319,696), and the like may be used. L-tryptophan-producing bacteria belonging to the genus *Escherichia* with an enhanced activity of the protein encoded by the yedA gene or the yddG gene may also be used (U.S. patent applications 2003/0148473 A1 and 2003/0157667 A1).

Examples of parent strains for deriving the L-tryptophan-producing bacteria of the present invention also include strains in which one or more activities are enhanced for the following enzymes: anthranilate synthase, phosphoglycerate dehydrogenase, and tryptophan synthase. The anthranilate synthase and phosphoglycerate dehydrogenase are both subject to feedback inhibition by L-tryptophan and L-serine, so a mutation desensitizing this feedback inhibition may be introduced into these enzymes. Specific examples of strains having such a mutation include *E. coli* SV164 which harbors desensitized anthranilate synthase and *E. coli* SV164 which has been transformed with the plasmid pGH5 (WO 94/08031), which contains a mutant serA gene encoding feedback-desensitized phosphoglycerate dehydrogenase.

Examples of parent strains for deriving the L-tryptophan-producing bacteria of the present invention also include strains which have been transformed with the tryptophan operon containing a gene encoding desensitized anthranilate synthase (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of α and β subunits which are encoded by the trpA and trpB genes, respectively. In addition, L-tryptophan-producing ability may be improved by enhancing expression of the isocitrate lyase-malate synthase operon (WO2005/103275).

L-Proline-Producing Bacteria

Examples of parent strains for deriving L-proline-producing bacteria of the present invention include, but are not limited to, strains belonging to the genus *Escherichia*, such as *E. coli* 702ilvA (VKPM B-8012) which is deficient in the ilvA gene and is able to produce L-proline (EP 1172433). The bacterium of the present invention may be improved by enhancing the expression of one or more genes involved in L-proline biosynthesis. Examples of such genes include the proB gene coding for glutamate kinase which is desensitized to feedback inhibition by L-proline (DE Patent 3127361). In addition, the bacterium of the present invention may be improved by enhancing the expression of one or more genes coding for proteins responsible for excreting L-amino acids from the bacterial cell. Such genes include the b2682 and b2683 (ygaZH genes) (EP1239041 A2).

Examples of bacteria belonging to the genus *Escherichia*, which are able to produce L-proline include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15$^{th}$ Miami winter symposium, 1983, p. 34), and the like.

L-Arginine-Producing Bacteria

Examples of parent strains for deriving L-arginine-producing bacteria of the present invention include, but are not limited to, strains belonging to the genus *Escherichia*, such as *E. coli* strain 237 (VKPM B-7925) (U.S. Patent Application 2002/058315 A1) and its derivative strains harboring mutant N-acetylglutamate synthase (Russian Patent Application No. 2001112869), *E. coli* strain 382 (VKPM B-7926) (EP1170358A1), an arginine-producing strain transformed with the argA gene encoding N-acetylglutamate synthetase (EP1170361A1), and the like.

Examples of parent strains for deriving L-arginine producing bacteria of the present invention also include strains in which expression of one or more genes encoding an L-arginine biosynthetic enzyme are enhanced. Examples of such genes include genes encoding N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-Valine-Producing Bacteria

Example of parent strains for deriving L-valine-producing bacteria of the present invention include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by L-valine that is produced. Furthermore, the ilvA gene in the operon is desirably disrupted so that threonine deaminase activity is decreased.

Examples of parent strains for deriving L-valine-producing bacteria of the present invention include also include mutants having a mutation of amino-acyl t-RNA synthetase (U.S. Pat. No. 5,658,766). For example, E. coli VL1970, which has a mutation in the ileS gene encoding isoleucine tRNA synthetase, can be used. E. coli VL1970 has been deposited in the Russian National Collection of Industrial Microorganisms (VKPM) (Russia, 113545 Moscow, 1 Dorozhny Proezd, 1) on Jun. 24, 1988 under accession number VKPM B-4411.

Furthermore, mutants requiring lipoic acid for growth and/or lacking $H^+$-ATPase can also be used as parent strains (WO96/06926).

L-Isoleucine-Producing Bacteria

Examples of parent strains for deriving L-isoleucine producing bacteria of the present invention include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as parent strains (JP 2-458 A, FR 0356739, and U.S. Pat. No. 5,998,178).

2. Method of the Present Invention

The method of the present invention is a method for producing an L-amino acid by cultivating the bacterium of the present invention in a culture medium to produce and excrete the L-amino acid into the medium, and collecting the L-amino acid from the medium.

In the present invention, the cultivation, collection, and purification of an L-amino acid from the medium and the like may be performed in a manner similar to conventional fermentation methods wherein an amino acid is produced using a bacterium.

The medium used for culture may be either synthetic or natural, so long as it includes a carbon source, a nitrogen source, minerals and, if necessary, appropriate amounts of nutrients which the bacterium requires for growth. The carbon source may include various carbohydrates such as glucose and sucrose, and various organic acids. Depending on the mode of assimilation of the chosen microorganism, alcohol, including ethanol and glycerol, may be used. As the nitrogen source, various ammonium salts such as ammonia and ammonium sulfate, other nitrogen compounds such as amines, a natural nitrogen source such as peptone, soybean-hydrolysate, and digested fermentative microorganism can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation is preferably performed under aerobic conditions, such as a shaking culture, and a stirring culture with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to accumulation of the target L-amino acid in the liquid medium.

After cultivation, solids such as cells can be removed from the liquid medium by centrifugation or membrane filtration, and then the L-amino acid can be collected and purified by ion-exchange, concentration, and/or crystallization methods.

EXAMPLES

The present invention will be more concretely explained below with reference to the following non-limiting Examples.

Example 1

Preparation of the PCR Template and Helper Plasmids

The PCR template plasmid pMW118-attL-Cm-attR and the helper plasmid pMW-intxis-ts were prepared as follows:

(1) pMW118-attL-Cm-attR

The pMW118-attL-Cm-attR plasmid was constructed on the basis of pMW118-attL-Tc-attR that was obtained by ligation of the following four DNA fragments:

1) the BglII-EcoRI fragment (114 bp) carrying attL (SEQ ID NO: 3) which was obtained by PCR amplification of the corresponding region of the E. coli W3350 (contained λ prophage) chromosome using oligonucleotides P1 and P2 (SEQ ID NOS: 4 and 5) as primers (these primers contained the subsidiary recognition sites for BglII and EcoRI endonucleases);

2) the PstI-HindIII fragment (182 bp) carrying attR (SEQ ID NO: 6) which was obtained by PCR amplification of the corresponding region of the E. coli W3350 (contained λ prophage) chromosome using the oligonucleotides P3 and P4 (SEQ ID NOS: 7 and 8) as primers (these primers contained the subsidiary recognition sites for PstI and HindIII endonucleases);

3) the large BglII-HindIII fragment (3916 bp) of pMW118-ter_rrnB. The plasmid pMW118-ter_rrnB was obtained by ligation of the following three DNA fragments:

the large DNA fragment (2359 bp) carrying the AatII-EcoRI fragment of pMW118 that was obtained by the following way: pMW118 was digested with EcoRI restriction endonuclease, treated with Klenow fragment of DNA polymerase I, and then digested with AatII restriction endonuclease;

the small AatII-BglII fragment (1194 bp) of pUC19 carrying the bla gene for ampicillin resistance ($Ap^R$) was obtained by PCR amplification of the corresponding region of the pUC19 plasmid using oligonucleotides P5 and P6 (SEQ ID NOS: 9 and 10) as primers (these primers contained the subsidiary recognition sites for AatII and BglII endonucleases);

the small BglII-PstI fragment (363 bp) of the transcription terminator ter_rrnB was obtained by PCR amplification of the corresponding region of the E. coli MG1655 chromosome using oligonucleotides P7 and P8 (SEQ ID NOS: 11 and 12) as primers (these primers contained the subsidiary recognition sites for BglII and PstI endonucleases);

4) the small EcoRI-PstI fragment (1388 bp) (SEQ ID NO: 13) of pML-Tc-ter_thrL bearing the tetracycline resistance gene and the ter_thrL transcription terminator; the pML-Tc-ter_thrL plasmid was obtained in two steps:

the pML-ter_thrL plasmid was obtained by digesting the pML-MCS plasmid (Mashko, S. V. et al., Biotekhnologiya (in Russian), 2001, no. 5, 3-20) with the XbaI and BamHI restriction endonucleases, followed by ligation of the large fragment (3342 bp) with the XbaI-BamHI fragment (68 bp) carrying terminator ter_thrL obtained by PCR amplification of the corresponding region of the E. coli MG1655 chromosome using oligonucleotides P9 and P10 (SEQ ID NOS: 14 and 15) as primers (these primers contained the subsidiary recognition sites for the XbaI and BamHI endonucleases);

the pML-Tc-ter_thrL plasmid was obtained by digesting the pML-ter_thrL plasmid with the KpnI and XbaI restriction endonucleases followed by treatment with Klenow fragment of DNA polymerase I and ligation with the small EcoRI-Van91I fragment (1317 bp) of pBR322 bearing the tetracycline resistance gene (pBR322 was digested with EcoRI and Van91I restriction endonucleases and then treated with Klenow fragment of DNA polymerase I);

The above strain E. coli W3350 is a derivative of wild-type strain E. coli K-12. The strain E. coli MG1655 (ATCC 700926) is a wild-type strain and can be obtained from American Type Culture Collection (P.O. Box 1549 Manassas, Va. 20108, United States of America). The plasmid pMW118 and pUC19 are commercially available. The BglII-EcoRI fragment carrying attL and the BglII-PstI fragment of the transcription terminator ter_rrnB can be obtained from the other strain of E. coli in the same manner as describe above.

The pMW118-attL-Cm-attR plasmid was constructed by ligation of the large BamHI-XbaI fragment (4413 bp) of pMW118-attL-Tc-attR and the artificial DNA BglII-XbaI fragment (1162 bp) containing the $P_{A2}$ promoter (the early promoter of the phage T7), the cat gene for chloramphenicol resistance ($Cm^R$), the ter_thrL transcription terminator, and attR. The artificial DNA fragment (SEQ ID NO: 16) was obtained as follows:

1. The pML-MCS plasmid was digested with the KpnI and XbaI restriction endonucleases and ligated with the small KpnI-XbaI fragment (120 bp), which included the $P_{A2}$ promoter (the early promoter of phage T7) obtained by PCR amplification of the corresponding DNA region of phage T7 using oligonucleotides P11 and P12 (SEQ ID NOS: 17 and 18, respectively) as primers (these primers contained the subsidiary recognition sites for KpnI and XbaI endonucleases). As a result, the pML-$P_{A2}$-MCS plasmid was obtained. The complete nucleotide sequence of phage T7 has been reported (J. Mol. Biol., 166: 477-535 (1983).

2. The XbaI site was deleted from pML-$P_{A2}$-MCS. As a result, the pML-$P_{A2}$-MCS(XbaI$^-$) plasmid was obtained.

3. The small BglII-HindIII fragment (928 bp) of pML-$P_{A2}$-MCS(XbaI$^-$) containing the $P_{A2}$ promoter (the early promoter of the phage T7) and the cat gene for chloramphenicol resistance ($Cm^R$) was ligated with the small HindIII-HindIII fragment (234 bp) of pMW118-attL-Tc-attR containing the ter_thrL transcription terminator and attR.

4. The required artificial DNA fragment (1156 bp) was obtained by PCR amplification of the ligation reaction mixture using oligonucleotides P9 and P4 (SEQ ID NOS: 14 and 8) as primers (these primers contained the subsidiary recognition sites for HindIII and XbaI endonucleases).

(2) pMW-intxis-ts

Recombinant plasmid pMW-intxis-ts containing the cI repressor gene and the int-xis genes of phage λ under the control of promoter $P_R$ was constructed on the basis of vector pMWP$_{lac}$lacI-ts. To construct the pMWP$_{lac}$lacI-ts variant, the AatII-EcoRV fragment of the pMWP$_{lac}$lacI plasmid (Skorokhodova, A. Yu. et al., Biotekhnologiya (in Russian), 2004, no. 5, 3-21) was substituted with the AatII-EcoRV fragment of the pMAN997 plasmid (Tanaka, K. et al., J. Bacteriol., 2001, 183(22): 6538-6542, WO99/03988) bearing the par and ori loci and the repA$^{ts}$ gene (a temperature sensitive-replication origin) of the pSC101 replicon. The plasmid pMAN997 was constructed by exchanging the VspI-HindIII fragments of pMAN031 (J. Bacteriol., 162, 1196 (1985)) and pUC19.

Two DNA fragments were amplified using phage λ DNA ("Fermentas") as a template. The first one contained the DNA sequence from 37,168 to 38,046, the cI repressor gene, promoters $P_{RM}$ and $P_R$, and the leader sequence of the cro gene. This fragment was PCR-amplified using oligonucleotides P13 and P14 (SEQ ID NOS: 19 and 20) as primers. The second DNA fragment containing the xis-int genes of phage λ and the DNA sequence from 27801 to 29100 was PCR-amplified using oligonucleotides P15 and P16 (SEQ ID NOS: 21 and 22) as primers. All primers contained the corresponding restriction sites.

The first PCR-amplified fragment carrying the cI repressor was digested with restriction endonuclease ClaI, treated with Klenow fragment of DNA polymerase I, and then digested with restriction endonuclease EcoRI. The second PCR-amplified fragment was digested with restriction endonucleases EcoRI and PstI. The pMWP$_{lac}$lacI-ts plasmid was digested with the BglII endonuclease, treated with Klenow fragment of DNA polymerase I, and digested with the PstI restriction endonuclease. The vector fragment of pMWP$_{lac}$lacI-ts was eluted from agarose gel and ligated with the above-mentioned digested PCR-amplified fragments to obtain the pMW-intxis-ts recombinant plasmid.

Example 2

Construction of a Strain with an Inactivated ybiV Gene

1. Deletion of the ybiV Gene

A strain in which the ybiV gene had been deleted was constructed by the method initially developed by Datsenko, K. A. and Wanner, B. L. (Proc. Natl. Acad. Sci. USA, 2000, 97(12): 6640-6645) called "Red-driven integration". The DNA fragment containing the Cm$^R$ marker encoded by the cat gene was obtained by PCR, using primers P17 (SEQ ID NO: 23) and P18 (SEQ ID NO: 24) and plasmid pMW118-attL-Cm-attR as a template (for construction see Example 1). Primer P17 contains both a region complementary to the 36-nt region located at the 5' end of the ybiV gene and a region complementary to the attL region. Primer P18 contains both a region complementary to the 35-nt region located at the 3' end of the ybiV gene and a region complementary to the attR region. Conditions for PCR were as follows: denaturation step: 3 min at 95° C.; profile for two first cycles: 1 min at 95°

C., 30 sec at 50° C., 40 sec at 72° C.; profile for the last 25 cycles: 30 sec at 95° C., 30 sec at 54° C., 40 sec at 72° C.; final step: 5 min at 72° C.

Figure 2:
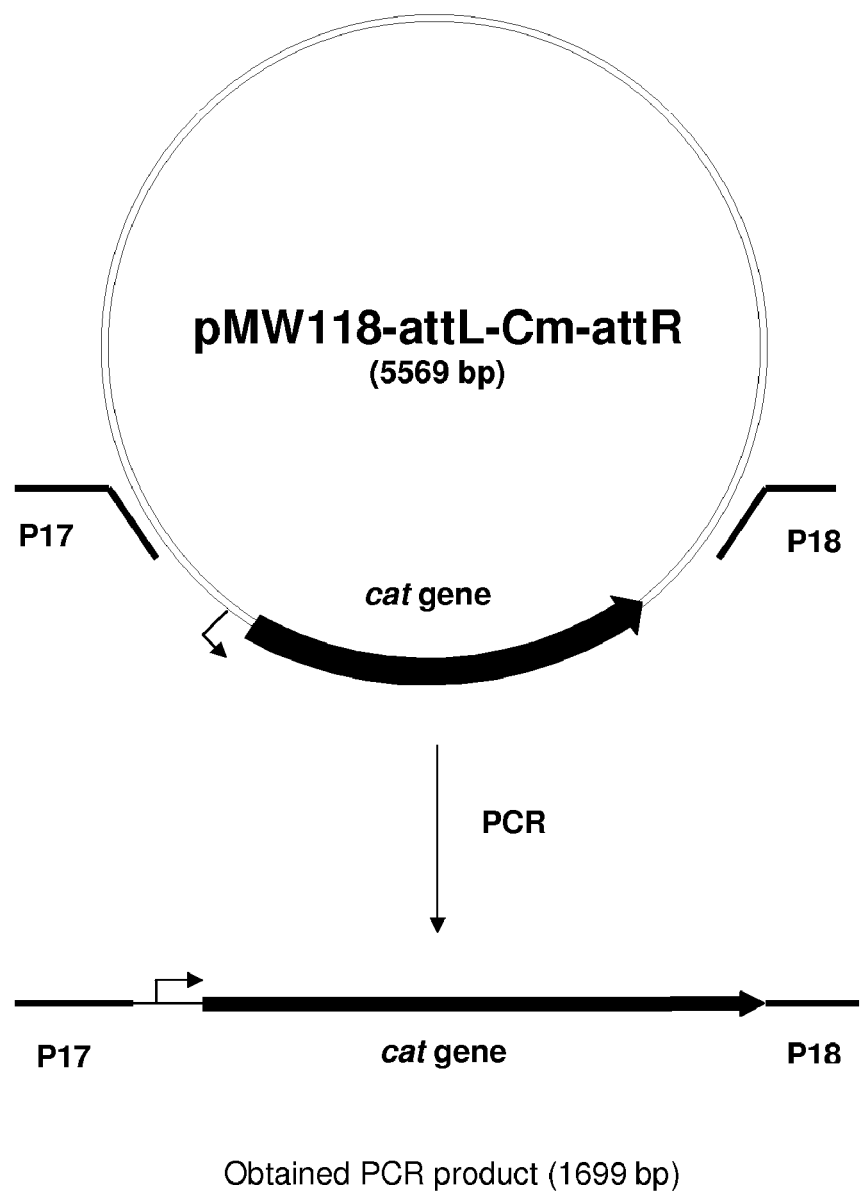
FIG. 2 shows the relative positions of primers P17 and P18 on plasmid pMW118-attL-Cm-attR used for PCR amplification of the cat gene.

A 1699-bp PCR product (FIG. 2) was obtained and purified in agarose gel and was used for electroporation of *E. coli* MG1655 (ATCC 700926), which contains the pKD46 plasmid having a temperature-sensitive replication origin. The pKD46 plasmid (Datsenko, K. A. and Wanner, B. L., Proc. Natl. Acad. Sci. USA, 2000, 97(12):6640-6645) includes a 2,154-bp DNA fragment of phage λ (nucleotide positions 31088 to 33241, GenBank accession no. J02459), and contains genes of the λ Red homologous recombination system (γ, β, exo genes) under the control of the arabinose-inducible $P_{araB}$ promoter. The plasmid pKD46 is necessary for integration of the PCR product into the chromosome of strain MG1655. The strain MG1655 can be obtained from American Type Culture Collection. (P.O. Box 1549 Manassas, Va. 20108, U.S.A.).

Electrocompetent cells were prepared as follows: *E. coli* MG1655 was grown at 30° C. in LB medium containing ampicillin (100 mg/l), and the culture was diluted 100 times with 5 ml of SOB medium (Sambrook et al, "Molecular Cloning: A Laboratory Manual, Second Edition", Cold Spring Harbor Laboratory Press, 1989) with ampicillin and L-arabinose (1 mM). The cells were grown with aeration at 30° C. to an $OD_{600}$ of ≈0.6 and then were made electrocompetent by concentrating 100-fold, and washing three times with ice-cold deionized $H_2O$. Electroporation was performed using 70 μl of cells and ≈100 ng of the PCR product. Cells after electroporation were incubated with 1 ml of SOC medium (Sambrook et al, "Molecular Cloning: A Laboratory Manual, Second Edition", Cold Spring Harbor Laboratory Press, 1989) at 37° C. for 2.5 hours and then were plated onto L-agar containing chloramphenicol (30 μg/ml) and were grown at 37° C. to select $Cm^R$ recombinants. Then, to eliminate the pKD46 plasmid, two passages on L-agar with Cm at 42° C. were performed and the resulting colonies were tested for sensitivity to ampicillin.

2. Verification of the ybiV Gene Deletion by PCR

Figure 3:
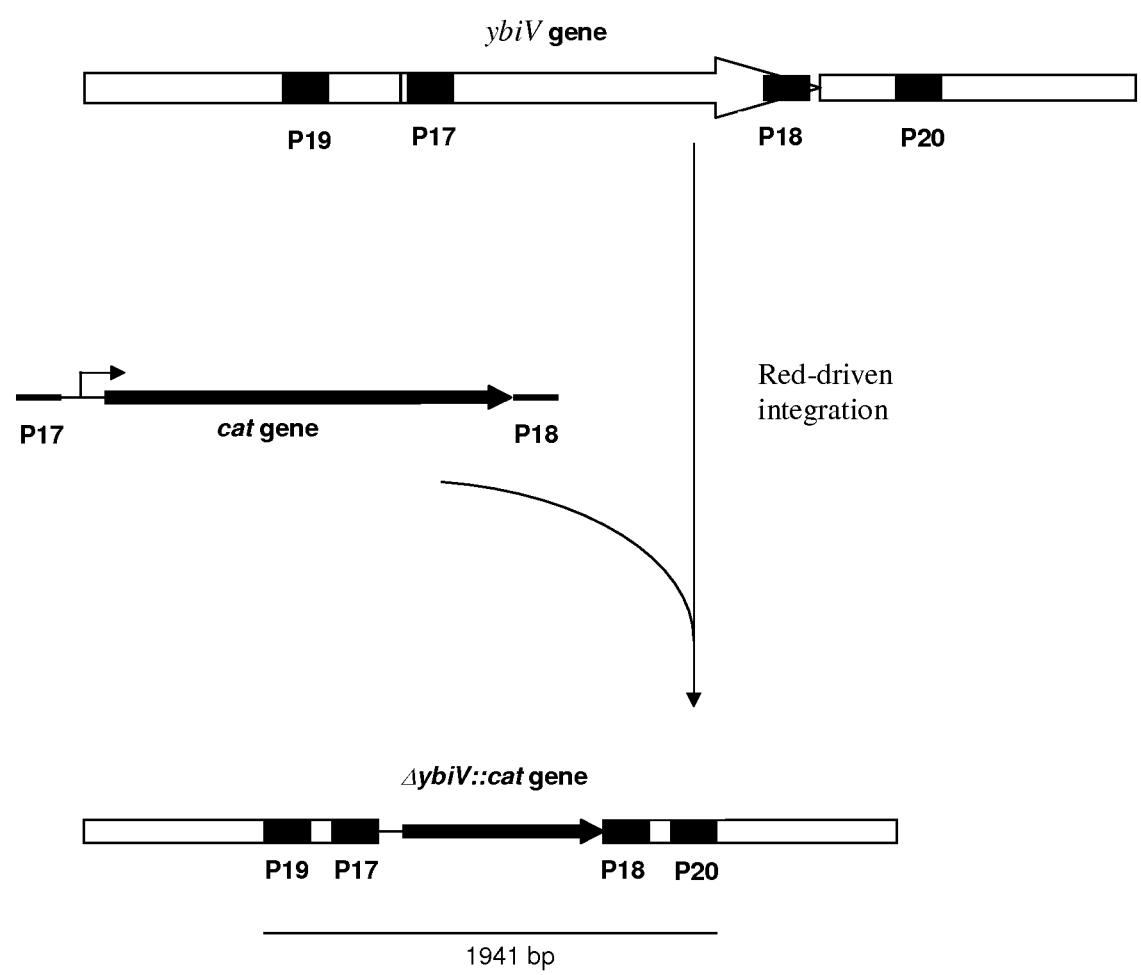
FIG. 3 shows the construction of the chromosomal DNA fragment which includes the inactivated ybiV gene.

The mutants having the ybiV gene deleted and marked with the Cm resistance gene were verified by PCR. Locus-specific primers P19 (SEQ ID NO: 25) and P20 (SEQ ID NO: 26) were used in PCR for the verification. Conditions for PCR verification were as follows: denaturation step: 3 min at 94° C.; profile for 30 cycles: 30 sec at 94° C., 30 sec at 54° C., 1 min at 72° C.; final step: 7 min at 72° C. The PCR product obtained in the reaction with the parental ybiV MG1655 strain as a template was 945 bp in length. The PCR product obtained in the reaction with the mutant strain as the template was 1941 bp in length (FIG. 3). The mutant strain was named MG1655 ΔybiV::cat.

Example 3

Production of L-Threonine by *E. coli* B-3996-ΔybiV

To test the effect of inactivation of the ybiV gene on threonine production, DNA fragments from the chromosome of the above-described *E. coli* strain MG1655 ΔybiV::cat were transferred to the threonine-producing *E. coli* strain VKPM B-3996 by P1 transduction (Miller, J. H. Experiments in Molecular Genetics, Cold Spring Harbor Lab. Press, 1972, Plainview, N.Y.) to obtain the strain B-3996-ΔybiV.

Both *E. coli* strains, B-3996 and B-3996-ΔybiV, were grown for 18-24 hours at 37° C. on L-agar plates. To obtain a seed culture, the strains were grown on a rotary shaker (250 rpm) at 32° C. for 18 hours in 20×200-mm test tubes containing 2 ml of L-broth supplemented with 4% glucose. Then, the fermentation medium was inoculated with 0.21 ml (10%) of seed material. The fermentation was performed in 2 ml of minimal medium for fermentation in 20×200-mm test tubes. Cells were grown for 65 hours at 32° C. with shaking at 250 rpm.

After cultivation, the amount of L-threonine which had accumulated in the medium was determined by paper chromatography using the following mobile phase: butanol-acetic acid-water=4:1:1 (v/v). A solution of ninhydrin (2%) in acetone was used as a visualizing reagent. A spot containing L-threonine was cut out, L-threonine was eluted with 0.5% water solution of $CdCl_2$, and the amount of L-threonine was estimated spectrophotometrically at 540 nm. The results of ten independent test tube fermentations are shown in Table 1.

The composition of the fermentation medium (g/l) was as follows:

| | |
|---|---|
| Glucose | 80.0 |
| $(NH_4)_2SO_4$ | 22.0 |
| NaCl | 0.8 |
| $KH_2PO_4$ | 2.0 |
| $MgSO_4 \cdot 7H_2O$ | 0.8 |
| $FeSO_4 \cdot 7H_2O$ | 0.02 |
| $MnSO_4 \cdot 5H_2O$ | 0.02 |
| Thiamine HCl | 0.0002 |
| Yeast extract | 1.0 |
| $CaCO_3$ | 30.0 |

Glucose and magnesium sulfate were sterilized separately. $CaCO_3$ was sterilized by dry-heat at 180° C. for 2 hours. The pH was adjusted to 7.0. The antibiotic was introduced into the medium after sterilization.

TABLE 1

| Strain | $OD_{540}$ | Amount of L-threonine, g/l |
|---|---|---|
| B-3996 | 32.1 ± 0.6 | 21.3 ± 0.2 |
| B-3996-ΔybiV | 30.9 ± 0.8 | 21.9 ± 0.3 |

As follows from Table 1, B-3996-ΔybiV caused accumulation of a higher amount of L-threonine, as compared with B-3996.

Example 4

Production of L-Lysine by *E. coli* WC196 (pCABD2)-ΔybiV

To test the effect of inactivation of the ybiV gene on lysine production, DNA fragments from the chromosome of the above-described *E. coli* strain MG1655 ΔybiV::cat can be transferred to the lysine-producing *E. coli* strain WC196 (pCABD2) by P1 transduction (Miller, J. H. Experiments in Molecular Genetics, Cold Spring Harbor Lab. Press, 1972, Plainview, N.Y.) to obtain WC196(pCABD2)-ΔybiV. The pCABD2 plasmid includes the dapA gene encoding dihydrodipicolinate synthase having a mutation which desensitizes feedback inhibition by L-lysine, the lysC gene encoding aspartokinase III having a mutation which desensitizes feedback inhibition by L-lysine, the dapB gene encoding dihydrodipicolinate reductase, and the ddh gene encoding diaminopimelate dehydrogenase (U.S. Pat. No. 6,040,160).

Both *E. coli* strains, WC196(pCABD2) and WC196 (pCABD2)-ΔybiV, can be cultured in L-medium containing streptomycin (20 mg/l) at 37° C., and 0.3 ml of the obtained culture can be inoculated into 20 ml of the fermentation medium containing the required drugs in a 500-ml flask. The cultivation can be carried out at 37° C. for 16 hours by using a reciprocal shaker at the agitation speed of 115 rpm. After the cultivation, the amounts of L-lysine and residual glucose in the medium can be measured by a known method (Biotech-analyzer AS210 manufactured by Sakura Seiki Co.). Then, the yield of L-lysine can be calculated relative to consumed glucose for each of the strains.

The composition of the fermentation medium (g/l) is as follows:

| | |
|---|---|
| Glucose | 40 |
| $(NH_4)_2SO_4$ | 24 |
| $K_2HPO_4$ | 1.0 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Yeast extract | 2.0 |

The pH is adjusted to 7.0 by KOH and the medium is autoclaved at 115° C. for 10 min. Glucose and $MgSO_4.7H_2O$ are sterilized separately. $CaCO_3$ is dry-heat sterilized at 180° C. for 2 hours and added to the medium for a final concentration of 30 g/l.

Example 5

Production of L-Cysteine by *E. coli* JM15(ydeD)-ΔybiV

To test the effect of inactivation of the ybiV gene on L-cysteine production, DNA fragments from the chromosome of the above-described *E. coli* strain MG1655 ΔybiV::cat can be transferred to the L-cysteine-producing *E. coli* strain JM15 (ydeD) by P1 transduction (Miller, J. H. Experiments in Molecular Genetics, Cold Spring Harbor Lab. Press, 1972, Plainview, N.Y.) to obtain the strain JM15(ydeD)-ΔybiV.

*E. coli* JM15(ydeD) is a derivative of *E. coli* JM15 (U.S. Pat. No. 6,218,168), which can be transformed with DNA having the ydeD gene encoding a membrane protein, and is not involved in a biosynthetic pathway of any L-amino acid (U.S. Pat. No. 5,972,663). The strain JM15 (CGSC#5042) can be obtained from The Coli Genetic Stock Collection at the *E. coli* Genetic Resource Center, MCD Biology Department, Yale University (http://cgsc.biology.yale.edu/).

Fermentation conditions for evaluation of L-cysteine production were described in detail in Example 6 of U.S. Pat. No. 6,218,168.

Example 6

Production of L-Leucine by *E. coli* 57-ΔybiV

To test the effect of inactivation of the ybiV gene on L-leucine production, DNA fragments from the chromosome of the above-described *E. coli* strain MG1655 ΔybiV::cat can be transferred to the L-leucine-producing *E. coli* strain 57 (VKPM B-7386, U.S. Pat. No. 6,124,121) by P1 transduction (Miller, J. H. Experiments in Molecular Genetics, Cold Spring Harbor Lab. Press, 1972, Plainview, N.Y.) to obtain the strain 57-ΔybiV. The strain 57 has been deposited in the Russian National Collection of Industrial Microorganisms (VKPM) (Russia, 117545 Moscow, 1 Dorozhny proezd, 1) on May 19, 1997 under accession number VKPM B-7386.

Both *E. coli* strains, 57 and 57-ΔybiV, can be cultured for 18-24 hours at 37° C. on L-agar plates. To obtain a seed culture, the strains can be grown on a rotary shaker (250 rpm) at 32° C. for 18 hours in 20×200-mm test tubes containing 2 ml of L-broth supplemented with 4% sucrose. Then, the fermentation medium can be inoculated with 0.21 ml of seed material (10%). The fermentation can be performed in 2 ml of a minimal fermentation medium in 20×200-mm test tubes. Cells can be grown for 48-72 hours at 32° C. with shaking at 250 rpm. The amount of L-leucine can be measured by paper chromatography (liquid phase composition: butanol-acetic acid-water=4:1:1).

The composition of the fermentation medium (g/l) (pH 7.2) is as follows:

| | |
|---|---|
| Glucose | 60.0 |
| $(NH_4)_2SO_4$ | 25.0 |
| $K_2HPO_4$ | 2.0 |
| $MgSO_4 \cdot 7H_2O$ | 1.0 |
| Thiamine | 0.01 |
| $CaCO_3$ | 25.0 |

Glucose and $CaCO_3$ are sterilized separately.

Example 7

Production of L-Histidine by *E. coli* 80-ΔybiV

To test the effect of inactivation of the ybiV gene on L-histidine production, DNA fragments from the chromosome of the above-described *E. coli* strain MG1655 ΔybiV::cat can be transferred to the histidine-producing *E. coli* strain 80 by P1 transduction (Miller, J. H. Experiments in Molecular Genetics, Cold Spring Harbor Lab. Press, 1972, Plainview, N.Y.) to obtain the strain 80-ΔybiV. The strain 80 has been described in Russian patent 2119536 and deposited in the Russian National Collection of Industrial Microorganisms (Russia, 117545 Moscow, 1 Dorozhny proezd, 1) on Oct. 15, 1999 under accession number VKPM B-7270 and then converted to a deposit under the Budapest Treaty on Jul. 12, 2004.

Both *E. coli* strains, 80 and 80-ΔybiV, can be cultured in L-broth for 6 hours at 29° C. Then, 0.1 ml of obtained cultures can each be inoculated into 2 ml of fermentation medium in a 20×200-mm test tube and cultivated for 65 hours at 29° C. with shaking on a rotary shaker (350 rpm). After cultivation, the amount of histidine which accumulates in the medium can be determined by paper chromatography. The paper can be developed with a mobile phase consisting of n-butanol:acetic acid:water=4:1:1 (v/v). A solution of ninhydrin (0.5%) in acetone can be used as a visualizing reagent.

The composition of the fermentation medium (g/l) (pH 6.0) is as follows:

| | |
|---|---|
| Glucose | 100.0 |
| Mameno (soybean hydrolysate) | 0.2 as total nitrogen |
| L-proline | 1.0 |
| $(NH_4)_2SO_4$ | 25.0 |
| $KH_2PO_4$ | 2.0 |
| $MgSO_4 \cdot 7H_2O$ | 1.0 |
| $FeSO_4 \cdot 7H_2O$ | 0.01 |
| $MnSO_4$ | 0.01 |
| Thiamine | 0.001 |
| Betaine | 2.0 |
| $CaCO_3$ | 60.0 |

Glucose, proline, betaine and CaCO₃ are sterilized separately. The pH is adjusted to 6.0 before sterilization.

Example 8

Production of L-Glutamate by E. coli VL334thrC⁺-ΔybiV

To test the effect of inactivation of the ybiV gene on L-glutamate production, DNA fragments from the chromosome of the above-described E. coli strain MG1655 ΔybiV::cat can be transferred to the L-glutamate-producing E. coli strain VL334thrC⁺ (EP 1172433) by P1 transduction (Miller, J. H. Experiments in Molecular Genetics, Cold Spring Harbor Lab. Press, 1972, Plainview, N.Y.) to obtain the strain VL334thrC⁺-ΔybiV. The strain VL334thrC⁺ has been deposited in the Russian National Collection of Industrial Microorganisms (VKPM) (Russia, 117545 Moscow, 1 Dorozhny proezd, 1) on Dec. 6, 2004 under the accession number VKPM B-8961 and then converted to a deposit under the Budapest Treaty on Dec. 8, 2004.

Both E. coli strains, VL334thrC⁺ and VL334thrC⁺-ΔybiV, can be grown for 18-24 hours at 37° C. on L-agar plates. Then, one loop of the cells can be transferred into test tubes containing 2 ml of fermentation medium. The fermentation medium contains glucose (60 g/l), ammonium sulfate (25 g/l), KH$_2$PO$_4$ (2 g/l), MgSO$_4$ (1 g/l), thiamine (0.1 mg/ml), L-isoleucine (70 μg/ml), and CaCO₃ (25 g/l). The pH is adjusted to 7.2. Glucose and CaCO₃ are sterilized separately. Cultivation can be carried out at 30° C. for 3 days with shaking. After the cultivation, the amount of L-glutamic acid which is produced can be determined by paper chromatography (liquid phase composition of butanol-acetic acid-water=4:1:1) with subsequent staining by ninhydrin (1% solution in acetone) and further elution of the compounds in 50% ethanol with 0.5% CdCl$_2$.

Example 9

Production of L-Phenylalanine by E. coli AJ12739-ΔybiV

To test the effect of inactivation of the ybiV gene on L-phenylalanine production, DNA fragments from the chromosome of the above-described E. coli strain MG1655 ΔybiV::cat can be transferred to the phenylalanine-producing E. coli strain AJ12739 by P1 transduction (Miller, J. H. Experiments in Molecular Genetics, Cold Spring Harbor Lab. Press, 1972, Plainview, N.Y.) to obtain the strain AJ12739-ΔybiV. The strain AJ12739 has been deposited in the Russian National Collection of Industrial Microorganisms (VKPM) (Russia, 117545 Moscow, 1 Dorozhny proezd, 1) on Nov. 6, 2001 under accession number VKPM B-8197 and then converted to a deposit under the Budapest Treaty on Aug. 23, 2002.

Both E. coli strains, AJ12739-ΔybiV and AJ12739, can be cultivated at 37° C. for 18 hours in a nutrient broth, and 0.3 ml of the obtained cultures can each be inoculated into 3 ml of a fermentation medium in a 20×200-mm test tube and cultivated at 37° C. for 48 hours with shaking on a rotary shaker. After cultivation, the amount of phenylalanine which accumulates in the medium can be determined by TLC. The 10×15-cm TLC plates coated with 0.11-mm layers of Sorbfil silica gel containing no fluorescent indicator (Stock Company Sorbpolymer, Krasnodar, Russia) can be used. The Sorbfil plates can be developed with a mobile phase consisting of propan-2-ol:ethylacetate:25% aqueous ammonia:water=40:40:7:16 (v/v). A solution of ninhydrin (2%) in acetone can be used as a visualizing reagent.

The composition of the fermentation medium (g/l) is as follows:

| | |
|---|---|
| Glucose | 40.0 |
| (NH$_4$)$_2$SO$_4$ | 16.0 |
| K$_2$HPO$_4$ | 0.1 |
| MgSO$_4$•7H$_2$O | 1.0 |
| FeSO$_4$•7H$_2$O | 0.01 |
| MnSO$_4$•5H$_2$O | 0.01 |
| Thiamine HCl | 0.0002 |
| Yeast extract | 2.0 |
| Tyrosine | 0.125 |
| CaCO$_3$ | 20.0 |

Glucose and magnesium sulfate are sterilized separately. CaCO₃ is dry-heat sterilized at 180° C. for 2 hours. The pH is adjusted to 7.0.

Example 10

Production of L-Tryptophan by E. coli SV164 (pGH5)-ΔybiV

To test the effect of inactivation of the ybiV gene on L-tryptophan production, DNA fragments from the chromosome of the above-described E. coli strain MG1655 ΔybiV::cat can be transferred to the tryptophan-producing E. coli strain SV164 (pGH5) by P1 transduction (Miller, J. H. Experiments in Molecular Genetics, Cold Spring Harbor Lab. Press, 1972, Plainview, N.Y.) to obtain the strain SV164(pGH5)-ΔybiV. The strain SV164 has the trpE allele encoding anthranilate synthase not subject to feedback inhibition by tryptophan. The plasmid pGH5 harbors a mutant serA gene encoding phosphoglycerate dehydrogenase not subject to feedback inhibition by serine. The strain SV164 (pGH5) is described in detail in U.S. Pat. No. 6,180,373.

Both E. coli strains, SV164(pGH5)-ΔybiV and SV164 (pGH5), can be cultivated with shaking at 37° C. for 18 hours in 3 ml of nutrient broth supplemented with tetracycline (20 mg/l, marker of pGH5 plasmid). The obtained cultures (0.3 ml each) can each be inoculated into 3 ml of a fermentation medium containing tetracycline (20 mg/l) in 20×200-mm test tubes, and cultivated at 37° C. for 48 hours with a rotary shaker at 250 rpm. After cultivation, the amount of tryptophan which accumulates in the medium can be determined by TLC as described in Example 8. The fermentation medium components are listed in Table 2, and are sterilized in separate groups (A, B, C, D, E, F, and H), as shown, to avoid adverse interactions during sterilization.

TABLE 2

| Solutions | Component | Final concentration, g/l |
|---|---|---|
| A | KH$_2$PO$_4$ | 1.5 |
| | NaCl | 0.5 |
| | (NH$_4$)$_2$SO$_4$ | 1.5 |
| | L-Methionine | 0.05 |
| | L-Phenylalanine | 0.1 |
| | L-Tyrosine | 0.1 |
| | Mameno (total N) | 0.07 |
| B | Glucose | 40.0 |
| | MgSO$_4$•7H$_2$O | 0.3 |
| C | CaCl$_2$ | 0.011 |
| D | FeSO$_4$•7H$_2$O | 0.075 |
| | Sodium citrate | 1.0 |
| E | Na$_2$MoO$_4$•2H$_2$O | 0.00015 |

TABLE 2-continued

| Solutions | Component | Final concentration, g/l |
|---|---|---|
|  | $H_3BO_3$ | 0.0025 |
|  | $CoCl_2 \cdot 6H_2O$ | 0.00007 |
|  | $CuSO_4 \cdot 5H_2O$ | 0.00025 |
|  | $MnCl_2 \cdot 4H_2O$ | 0.0016 |
|  | $ZnSO_4 \cdot 7H_2O$ | 0.0003 |
| F | Thiamine HCl | 0.005 |
| G | $CaCO_3$ | 30.0 |
| H | Pyridoxine | 0.03 |

Group A has pH 7.1 adjusted by $NH_4OH$. Each of groups A, B, C, D, E, F and H is sterilized separately, chilled, and mixed together, and then $CaCO_3$ sterilized by dry heat is added to the complete fermentation medium.

Example 11

Production of L-Proline by E. coli 702ilvA-ΔybiV

To test the effect of inactivation of the ybiV gene on L-proline production, DNA fragments from the chromosome of the above-described E. coli strain MG1655 ΔybiV::cat can be transferred to the proline-producing E. coli strain 702ilvA by P1 transduction (Miller, J. H. Experiments in Molecular Genetics, Cold Spring Harbor Lab. Press, 1972, Plainview, N.Y.) to obtain the strain 702ilvA-ΔybiV. The strain 702ilvA has been deposited in the Russian National Collection of Industrial Microorganisms (VKPM) (Russia, 117545 Moscow, 1 Dorozhny proezd, 1) on Jul. 18, 2000 under accession number VKPM B-8012 and then converted to a deposit under the Budapest Treaty on May 18, 2001.

Both E. coli strains, 702ilvA and 702ilvA-ΔybiV, can be grown for 18-24 hours at 37° C. on L-agar plates. Then, these strains can be cultivated under the same conditions as in Example 8.

Example 12

Production of L-Arginine by E. coli 382-ΔybiV

To test the effect of inactivation of the ybiV gene on L-arginine production, DNA fragments from the chromosome of the above-described E. coli strain MG1655 ΔybiV::cat were transferred to the arginine-producing E. coli strain 382 by P1 transduction (Miller, J. H. Experiments in Molecular Genetics, Cold Spring Harbor Lab. Press, 1972, Plainview, N.Y.) to obtain the strain 382-ΔybiV. The strain 382 has been deposited in the Russian National Collection of Industrial Microorganisms (VKPM) (Russia, 117545 Moscow, 1 Dorozhny proezd, 1) on Apr. 10, 2000 under accession number VKPM B-7926 and then converted to a deposit under the Budapest Treaty on May 18, 2001.

Both E. coli strains, 382-ΔybiV and 382, were cultivated with shaking at 37° C. for 18 hours in 3 ml of nutrient broth. The obtained cultures (0.3 ml each) were each inoculated into 3 ml of a fermentation medium in 20×200-mm test tubes and cultivated at 32° C. for 48 hours on a rotary shaker.

After the cultivation, the amount of L-arginine which had accumulated in the medium was determined by paper chromatography using the following mobile phase: butanol:acetic acid:water=4:1:1 (v/v). A solution of ninhydrin (2%) in acetone was used as a visualizing reagent. A spot containing L-arginine was cut out, L-arginine was eluted with 0.5% water solution of $CdCl_2$, and the amount of L-arginine was estimated spectrophotometrically at 540 nm. The results of ten independent test tube fermentations are shown in Table 3.

The composition of the fermentation medium (g/l) was as follows:

| | |
|---|---|
| Glucose | 48.0 |
| $(NH_4)_2SO_4$ | 35.0 |
| $KH_2PO_4$ | 2.0 |
| $MgSO_4 \cdot 7H_2O$ | 1.0 |
| Thiamine HCl | 0.0002 |
| Yeast extract | 1.0 |
| L-isoleucine | 0.1 |
| $CaCO_3$ | 5.0 |

Glucose and magnesium sulfate were sterilized separately. $CaCO_3$ was dry-heat sterilized at 180° C. for 2 hours. The pH was adjusted to 7.0.

TABLE 3

| Strain | $OD_{540}$ | Amount of L-arginine, g/l |
|---|---|---|
| 382 | 12.4 ± 0.8 | 11.6 ± 0.8 |
| 382-ΔybiV | 13.1 ± 0.9 | 12.6 ± 0.8 |

As follows from Table 3, strain 382-ΔybiV caused accumulation of a higher amount of L-arginine, as compared with strain 382.

Example 13

Elimination of Cm Resistance Gene (cat Gene) from the Chromosome of L-Amino Acid-Producing E. coli Strains The Cm resistance gene (cat gene) can be eliminated from the chromosome of the L-amino acid-producing strain using the int-xis system. For that purpose, an L-amino acid-producing strain having DNA fragments from the chromosome of the above-described E. coli strain MG1655 ΔybiV::cat transferred by P1 transduction (see Examples 3-12), can be transformed with plasmid pMWts-Int/Xis. Transformant clones can be selected on the LB-medium containing 100 μg/ml of ampicillin. Plates can be incubated overnight at 30° C. Transformant clones can be cured from the cat gene by spreading the separate colonies at 37° C. (at that temperature repressor CIts is partially inactivated and transcription of the int/xis genes is derepressed) followed by selection of $Cm^sAp^R$ variants. Elimination of the cat gene from the chromosome of the strain can be verified by PCR. Locus-specific primers P21 (SEQ ID NO: 27) and P22 (SEQ ID NO: 28) can be used in PCR for the verification. Conditions for PCR verification can be as described above. The PCR product obtained in reaction with cells having the eliminated cat gene as a template, should be 0.2 kbp in length. Thus, the L-amino acid-producing strain with the inactivated ybiV gene and eliminated cat gene can be obtained.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

INDUSTRIAL APPLICABILITY

According to the present invention, production of L-amino acid of a bacterium of the Enterobacteriaceae family can be enhanced.

The invention claimed is:

1. A method for producing an L-amino acid comprising: cultivating an L-amino acid-producing bacterium of the Enterobacteriaceae family in a medium to produce and excrete said L-amino acid into the medium, and collecting said L-amino acid from the medium, wherein said bacterium has been modified to attenuate expression of the ybiV gene on the chromosome of said bacterium.

2. The method according to claim 1, wherein said L-amino acid is selected from the group consisting of an aromatic L-amino acid and a non-aromatic L-amino acid.

3. The method according to claim 2, wherein said aromatic L-amino acid is selected from the group consisting of L-phenylalanine, L-tyrosine, and L-tryptophan.

4. The method according to claim 2, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine.

5. The method according to claim 1, wherein said expression of the ybiV gene is attenuated by inactivation of the ybiV gene.

6. The method according to claim 1, wherein said bacterium belongs to genus *Escherichia*.

7. The method according to claim 1, wherein said bacterium belongs to genus *Pantoea*.

* * * * *

SEQUENCE LISTING

<160> NUMBER OF SEQ ID NOS: 28

<210> SEQ ID NO 1
<211> LENGTH: 816
<212> TYPE: DNA
<213> ORGANISM: Escherichia coli
<220> FEATURE:
<221> NAME/KEY: CDS
<222> LOCATION: (1)..(816)

<400> SEQUENCE: 1

| | | | | | | | | | | | | | | | | |
|---|---|---|---|---|---|---|---|---|---|---|---|---|---|---|---|---|
| atg | agc | gta | aaa | gtt | atc | gtc | aca | gac | atg | gac | ggt | act | ttt | ctt | aac | 48 |
| Met | Ser | Val | Lys | Val | Ile | Val | Thr | Asp | Met | Asp | Gly | Thr | Phe | Leu | Asn | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gac | gcc | aaa | acg | tac | aac | caa | cca | cgt | ttt | atg | gcg | caa | tat | cag | gaa | 96 |
| Asp | Ala | Lys | Thr | Tyr | Asn | Gln | Pro | Arg | Phe | Met | Ala | Gln | Tyr | Gln | Glu | |
| | | | 20 | | | | | 25 | | | | | 30 | | | |

| | | | | | | | | | | | | | | | | |
|---|---|---|---|---|---|---|---|---|---|---|---|---|---|---|---|---|
| ctg | aaa | aag | cgc | ggc | att | aag | ttc | gtt | gtt | gcc | agc | ggt | aat | cag | tat | 144 |
| Leu | Lys | Lys | Arg | Gly | Ile | Lys | Phe | Val | Val | Ala | Ser | Gly | Asn | Gln | Tyr | |
| | | 35 | | | | | 40 | | | | | 45 | | | | |

| | | | | | | | | | | | | | | | | |
|---|---|---|---|---|---|---|---|---|---|---|---|---|---|---|---|---|
| tac | cag | ctt | att | tca | ttc | ttt | cct | gag | cta | aag | gat | gag | atc | tct | ttt | 192 |
| Tyr | Gln | Leu | Ile | Ser | Phe | Phe | Pro | Glu | Leu | Lys | Asp | Glu | Ile | Ser | Phe | |
| 50 | | | | | 55 | | | | | 60 | | | | | | |

| | | | | | | | | | | | | | | | | |
|---|---|---|---|---|---|---|---|---|---|---|---|---|---|---|---|---|
| gtc | gcg | gaa | aac | ggc | gca | ctg | gtt | tac | gaa | cat | ggc | aag | cag | ttg | ttc | 240 |
| Val | Ala | Glu | Asn | Gly | Ala | Leu | Val | Tyr | Glu | His | Gly | Lys | Gln | Leu | Phe | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| cac | ggc | gaa | ctg | acc | cga | cat | gaa | tcg | cgg | att | gtt | att | ggc | gag | ttg | 288 |
| His | Gly | Glu | Leu | Thr | Arg | His | Glu | Ser | Arg | Ile | Val | Ile | Gly | Glu | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| cta | aaa | gat | aag | caa | ctc | aat | ttt | gtc | gcc | tgc | ggt | ctg | caa | agt | gca | 336 |
| Leu | Lys | Asp | Lys | Gln | Leu | Asn | Phe | Val | Ala | Cys | Gly | Leu | Gln | Ser | Ala | |
| | | | 100 | | | | | 105 | | | | | 110 | | | |

| | | | | | | | | | | | | | | | | |
|---|---|---|---|---|---|---|---|---|---|---|---|---|---|---|---|---|
| tat | gtc | agc | gaa | aat | gcc | ccc | gaa | gca | ttt | gtc | gca | ctg | atg | gca | aaa | 384 |
| Tyr | Val | Ser | Glu | Asn | Ala | Pro | Glu | Ala | Phe | Val | Ala | Leu | Met | Ala | Lys | |
| | | 115 | | | | | 120 | | | | | 125 | | | | |

| | | | | | | | | | | | | | | | | |
|---|---|---|---|---|---|---|---|---|---|---|---|---|---|---|---|---|
| cac | tac | cat | cgc | ctg | aaa | cct | gta | aaa | gat | tat | cag | gag | att | gac | gac | 432 |
| His | Tyr | His | Arg | Leu | Lys | Pro | Val | Lys | Asp | Tyr | Gln | Glu | Ile | Asp | Asp | |
| | 130 | | | | | 135 | | | | | 140 | | | | | |

| | | | | | | | | | | | | | | | | |
|---|---|---|---|---|---|---|---|---|---|---|---|---|---|---|---|---|
| gta | ctg | ttc | aag | ttt | tcg | ctc | aac | ctg | ccg | gat | gaa | caa | atc | ccg | tta | 480 |
| Val | Leu | Phe | Lys | Phe | Ser | Leu | Asn | Leu | Pro | Asp | Glu | Gln | Ile | Pro | Leu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gtg | atc | gac | aaa | ctg | cac | gta | gcg | ctc | gat | ggc | att | atg | aaa | ccc | gtt | 528 |
| Val | Ile | Asp | Lys | Leu | His | Val | Ala | Leu | Asp | Gly | Ile | Met | Lys | Pro | Val | |
| | | | | 165 | | | | | 170 | | | | | 175 | | |

| | | | | | | | | | | | | | | | | |
|---|---|---|---|---|---|---|---|---|---|---|---|---|---|---|---|---|
| acc | agt | ggt | ttt | ggc | ttt | atc | gac | ctg | att | att | ccc | ggt | cta | cat | aaa | 576 |
| Thr | Ser | Gly | Phe | Gly | Phe | Ile | Asp | Leu | Ile | Ile | Pro | Gly | Leu | His | Lys | |
| | | | 180 | | | | | 185 | | | | | 190 | | | |

| | | | | | | | | | | | | | | | | |
|---|---|---|---|---|---|---|---|---|---|---|---|---|---|---|---|---|
| gca | aac | ggt | att | tcg | cgg | tta | ctg | aaa | cgc | tgg | gat | ctg | tca | ccg | caa | 624 |
| Ala | Asn | Gly | Ile | Ser | Arg | Leu | Leu | Lys | Arg | Trp | Asp | Leu | Ser | Pro | Gln | |
| | | 195 | | | | | 200 | | | | | 205 | | | | |

| | | | | | | | | | | | | | | | | |
|---|---|---|---|---|---|---|---|---|---|---|---|---|---|---|---|---|
| aat | gtg | gta | gcg | att | ggc | gac | agc | ggt | aac | gat | gcg | gag | atg | ctg | aaa | 672 |
| Asn | Val | Val | Ala | Ile | Gly | Asp | Ser | Gly | Asn | Asp | Ala | Glu | Met | Leu | Lys | |
| | 210 | | | | | 215 | | | | | 220 | | | | | |

| | | | | | | | | | | | | | | | | |
|---|---|---|---|---|---|---|---|---|---|---|---|---|---|---|---|---|
| atg | gcg | cgt | tat | tcc | ttt | gcg | atg | ggc | aat | gct | gcg | gaa | aac | att | aaa | 720 |
| Met | Ala | Arg | Tyr | Ser | Phe | Ala | Met | Gly | Asn | Ala | Ala | Glu | Asn | Ile | Lys | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| caa | atc | gcc | cgt | tac | gct | acc | gat | gat | aat | aat | cat | gaa | ggc | gcg | ctg | 768 |
| Gln | Ile | Ala | Arg | Tyr | Ala | Thr | Asp | Asp | Asn | Asn | His | Glu | Gly | Ala | Leu | |
| | | | | 245 | | | | | 250 | | | | | 255 | | |

| | | | | | | | | | | |
|---|---|---|---|---|---|---|---|---|---|---|
| aat | gtg | att | cag | gcg | gtg | ctg | gat | aac | aca | tcc | cct | ttt | aac | agc | tga | 816 |

```
Asn Val Ile Gln Ala Val Leu Asp Asn Thr Ser Pro Phe Asn Ser
            260                 265                 270

<210> SEQ ID NO 2
<211> LENGTH: 271
<212> TYPE: PRT
<213> ORGANISM: Escherichia coli

<400> SEQUENCE: 2

Met Ser Val Lys Val Ile Val Thr Asp Met Asp Gly Thr Phe Leu Asn
 1               5                  10                  15

Asp Ala Lys Thr Tyr Asn Gln Pro Arg Phe Met Ala Gln Tyr Gln Glu
            20                  25                  30

Leu Lys Lys Arg Gly Ile Lys Phe Val Val Ala Ser Gly Asn Gln Tyr
        35                  40                  45

Tyr Gln Leu Ile Ser Phe Phe Pro Glu Leu Lys Asp Glu Ile Ser Phe
    50                  55                  60

Val Ala Glu Asn Gly Ala Leu Val Tyr Glu His Gly Lys Gln Leu Phe
65                  70                  75                  80

His Gly Glu Leu Thr Arg His Glu Ser Arg Ile Val Ile Gly Glu Leu
                85                  90                  95

Leu Lys Asp Lys Gln Leu Asn Phe Val Ala Cys Gly Leu Gln Ser Ala
            100                 105                 110

Tyr Val Ser Glu Asn Ala Pro Glu Ala Phe Val Ala Leu Met Ala Lys
        115                 120                 125

His Tyr His Arg Leu Lys Pro Val Lys Asp Tyr Gln Glu Ile Asp Asp
    130                 135                 140

Val Leu Phe Lys Phe Ser Leu Asn Leu Pro Asp Glu Gln Ile Pro Leu
145                 150                 155                 160

Val Ile Asp Lys Leu His Val Ala Leu Asp Gly Ile Met Lys Pro Val
                165                 170                 175

Thr Ser Gly Phe Gly Phe Ile Asp Leu Ile Ile Pro Gly Leu His Lys
            180                 185                 190

Ala Asn Gly Ile Ser Arg Leu Leu Lys Arg Trp Asp Leu Ser Pro Gln
        195                 200                 205

Asn Val Val Ala Ile Gly Asp Ser Gly Asn Asp Ala Glu Met Leu Lys
    210                 215                 220

Met Ala Arg Tyr Ser Phe Ala Met Gly Asn Ala Ala Glu Asn Ile Lys
225                 230                 235                 240

Gln Ile Ala Arg Tyr Ala Thr Asp Asp Asn Asn His Glu Gly Ala Leu
                245                 250                 255

Asn Val Ile Gln Ala Val Leu Asp Asn Thr Ser Pro Phe Asn Ser
            260                 265                 270

<210> SEQ ID NO 3
<211> LENGTH: 120
<212> TYPE: DNA
<213> ORGANISM: Artificial
<220> FEATURE:
<223> OTHER INFORMATION: DNA fragment containing attL

<400> SEQUENCE: 3
agatcttgaa gcctgctttt ttatactaag ttggcattat aaaaaagcat tgcttatcaa      60
tttgttgcaa cgaacaggtc actatcagtc aaaataaaat cattatttga tttcgaattc     120

<210> SEQ ID NO 4
<211> LENGTH: 40
<212> TYPE: DNA
```

```
<213> ORGANISM: Artificial
<220> FEATURE:
<223> OTHER INFORMATION: primer P1

<400> SEQUENCE: 4
ctagtaagat cttgaagcct gctttttat actaagttgg                                40

<210> SEQ ID NO 5
<211> LENGTH: 41
<212> TYPE: DNA
<213> ORGANISM: Artificial
<220> FEATURE:
<223> OTHER INFORMATION: primer P2

<400> SEQUENCE: 5
atgatcgaat tcgaaatcaa ataatgattt tattttgact g                             41

<210> SEQ ID NO 6
<211> LENGTH: 184
<212> TYPE: DNA
<213> ORGANISM: Artificial
<220> FEATURE:
<223> OTHER INFORMATION: DNA fragment containing attR

<400> SEQUENCE: 6
ctgcagtctg ttacaggtca ctaataccat ctaagtagtt gattcatagt gactgcatat         60
gttgtgtttt acagtattat gtagtctgtt ttttatgcaa aatctaattt aatatattga        120
tatttatatc attttacgtt tctcgttcag cttttttata ctaacttgag cgtctagaaa        180
gctt                                                                    184

<210> SEQ ID NO 7
<211> LENGTH: 41
<212> TYPE: DNA
<213> ORGANISM: Artificial
<220> FEATURE:
<223> OTHER INFORMATION: primer P3

<400> SEQUENCE: 7
atgccactgc agtctgttac aggtcactaa taccatctaa g                             41

<210> SEQ ID NO 8
<211> LENGTH: 46
<212> TYPE: DNA
<213> ORGANISM: Artificial
<220> FEATURE:
<223> OTHER INFORMATION: primer P4

<400> SEQUENCE: 8
accgttaagc tttctagacg ctcaagttag tataaaaaag ctgaac                        46

<210> SEQ ID NO 9
<211> LENGTH: 38
<212> TYPE: DNA
<213> ORGANISM: Artificial
<220> FEATURE:
<223> OTHER INFORMATION: primer P5

<400> SEQUENCE: 9
ttcttagacg tcaggtggca cttttcgggg aaatgtgc                                 38

<210> SEQ ID NO 10
<211> LENGTH: 37
<212> TYPE: DNA
<213> ORGANISM: Artificial
<220> FEATURE:
```

<223> OTHER INFORMATION: primer P6

<400> SEQUENCE: 10
taacagagat ctcgcgcaga aaaaaaggat ctcaaga                            37

<210> SEQ ID NO 11
<211> LENGTH: 46
<212> TYPE: DNA
<213> ORGANISM: Artificial
<220> FEATURE:
<223> OTHER INFORMATION: primer P7

<400> SEQUENCE: 11
aacagagatc taagcttaga tcctttgcct ggcggcagta gcgcgg                  46

<210> SEQ ID NO 12
<211> LENGTH: 35
<212> TYPE: DNA
<213> ORGANISM: Artificial
<220> FEATURE:
<223> OTHER INFORMATION: primer P8

<400> SEQUENCE: 12
ataaactgca gcaaaaagag tttgtagaaa cgcaa                              35

<210> SEQ ID NO 13
<211> LENGTH: 1388
<212> TYPE: DNA
<213> ORGANISM: Artificial
<220> FEATURE:
<223> OTHER INFORMATION: DNA fragment containing Tc gene and ter_thrL

<400> SEQUENCE: 13
gaattctcat gtttgacagc ttatcatcga taagctttaa tgcggtagtt tatcacagtt    60
aaattgctaa cgcagtcagg caccgtgtat gaaatctaac aatgcgctca tcgtcatcct   120
cggcaccgtc accctggatg ctgtaggcat aggcttggtt atgccggtac tgccgggcct   180
cttgcgggat atcgtccatt ccgacagcat cgccagtcac tatggcgtgc tgctagcgct   240
atatgcgttg atgcaatttc tatgcgcacc cgttctcgga gcactgtccg accgctttgg   300
ccgccgccca gtcctgctcg cttcgctact tggagccact atcgactacg cgatcatggc   360
gaccacaccc gtcctgtgga tcctctacgc cggacgcatc gtggccggca tcaccggcgc   420
cacaggtgcg gttgctggcg cctatatcgc cgacatcacc gatggggaag atcgggctcg   480
ccacttcggg ctcatgagcg cttgtttcgg cgtgggtatg gtggcaggcc ccgtggccgg   540
gggactgttg ggcgccatct ccttgcatgc accattcctt gcggcggcgg tgctcaacgg   600
cctcaaccta ctactgggct gcttcctaat gcaggagtcg cataagggag agcgtcgacc   660
gatgcccttg agagccttca acccagtcag ctccttccgg tgggcgcggg gcatgactat   720
cgtcgccgca cttatgactg tcttctttat catgcaactc gtaggacagg tgccggcagc   780
gctctgggtc attttcggcg aggaccgctt tcgctggagc gcgacgatga tcggcctgtc   840
gcttgcggta ttcggaatct tgcacgccct cgctcaagcc ttcgtcactg gtcccgccac   900
caaacgtttc ggcgagaagc aggccattat cgccggcatg gcggccgacg cgctgggcta   960
cgtcttgctg gcgttcgcga cgcgaggctg atggccttc cccattatga ttcttctcgc   1020
ttccggcggc atcgggatgc ccgcgttgca ggccatgctg tccaggcagg tagatgacga   1080
ccatcaggga cagcttcaag gatcgctcgc ggctcttacc agcctaactt cgatcactgg   1140
accgctgatc gtcacggcga tttatgccgc ctcggcgagc acatggaacg ggttggcatg   1200

-continued

| gattgtaggc gccgccctat accttgtctg cctccccgcg ttgcgtcgcg gtgcatggag | 1260 |
| --- | --- |
| ccgggccacc tcgacctgaa tggaagccgg cggcacctcg ctaacggatt caccactcca | 1320 |
| actagaaagc ttaacacaga aaaagcccg cacctgacag tgcgggcttt ttttttcgac | 1380 |
| cactgcag | 1388 |

```
<210> SEQ ID NO 14
<211> LENGTH: 36
<212> TYPE: DNA
<213> ORGANISM: Artificial
<220> FEATURE:
<223> OTHER INFORMATION: primer P9

<400> SEQUENCE: 14
```

| agtaattcta gaaagcttaa cacagaaaaa agcccg | 36 |
| --- | --- |

```
<210> SEQ ID NO 15
<211> LENGTH: 43
<212> TYPE: DNA
<213> ORGANISM: Artificial
<220> FEATURE:
<223> OTHER INFORMATION: primer P10

<400> SEQUENCE: 15
```

| ctagtaggat ccctgcagtg gtcgaaaaaa aaagcccgca ctg | 43 |
| --- | --- |

```
<210> SEQ ID NO 16
<211> LENGTH: 1162
<212> TYPE: DNA
<213> ORGANISM: Artificial
<220> FEATURE:
<223> OTHER INFORMATION: DNA fragment containing Pa2 promoter

<400> SEQUENCE: 16
```

| agatctccgg ataagtagac agcctgataa gtcgcacgaa aaacaggtat tgacaacatg | 60 |
| --- | --- |
| aagtaacatg cagtaagata caaatcgcta ggtaacacta gcagcgtcaa ccgggcgctc | 120 |
| tagctagagc caagctagct tggccggatc cgagattttc aggagctaag gaagctaaaa | 180 |
| tggagaaaaa aatcactgga tataccaccg ttgatatatc ccaatggcat cgtaaagaac | 240 |
| attttgaggc atttcagtca gttgctcaat gtacctataa ccagaccgtt cagctggata | 300 |
| ttacggcctt tttaaagacc gtaaagaaaa ataagcacaa gttttatccg gcctttattc | 360 |
| acattcttgc ccgcctgatg aatgctcatc cggaattccg tatggcaatg aaagacggtg | 420 |
| agctggtgat atgggatagt gttcacccct tgttacaccg ttttccatga gcaaactgaaa | 480 |
| cgttttcatc gctctggagt gaataccacg acgatttccg gcagtttcta cacatatatt | 540 |
| cgcaagatgt ggcgtgttac ggtgaaaacc tggcctattt ccctaaaggg tttattgaga | 600 |
| atatgttttt cgtctcagcc aatccctggg tgagtttcac cagttttgat ttaaacgtgg | 660 |
| ccaatatgga caacttcttc gcccccgttt tcaccatggg caaatattat acgcaaggcg | 720 |
| acaaggtgct gatgccgctg gcgattcagg ttcatcatgc cgtctgtgat ggcttccatg | 780 |
| tcggcagaat gcttaatgaa ttacaacagt actgcgatga gtggcagggc ggggcgtaat | 840 |
| ttttttaagg cagttattgg tgcccttaaa cgcctggtgc tacgcctgaa taagtgataa | 900 |
| taagcggatg aatggcagaa attcgtcgaa gcttaacaca gaaaaaagcc cgcacctgac | 960 |
| agtgcgggct ttttttttcg accactgcag tctgttacag gtcactaata ccatctaagt | 1020 |
| agttgattca tagtgactgc atatgttgtg tttacagta ttatgtagtc tgttttttat | 1080 |
| gcaaaatcta atttaatata ttgatattta tatcatttta cgtttctcgt tcagcttttt | 1140 |

-continued tatactaact tgagcgtcta ga                                              1162

<210> SEQ ID NO 17
<211> LENGTH: 37
<212> TYPE: DNA
<213> ORGANISM: Artificial
<220> FEATURE:
<223> OTHER INFORMATION: primer P11

<400> SEQUENCE: 17
atcgaggtac cagatctccg gataagtaga cagcctg                              37

<210> SEQ ID NO 18
<211> LENGTH: 32
<212> TYPE: DNA
<213> ORGANISM: Artificial
<220> FEATURE:
<223> OTHER INFORMATION: primer P12

<400> SEQUENCE: 18
gaaggtctag agcgcccggt tgacgctgct ag                                   32

<210> SEQ ID NO 19
<211> LENGTH: 27
<212> TYPE: DNA
<213> ORGANISM: Artificial
<220> FEATURE:
<223> OTHER INFORMATION: primer P13

<400> SEQUENCE: 19
ctaatatcga tgaagattct tgctcaa                                         27

<210> SEQ ID NO 20
<211> LENGTH: 34
<212> TYPE: DNA
<213> ORGANISM: Artificial
<220> FEATURE:
<223> OTHER INFORMATION: primer P14

<400> SEQUENCE: 20
gcgttgaatt ccatacaacc tccttagtac atgc                                 34

<210> SEQ ID NO 21
<211> LENGTH: 34
<212> TYPE: DNA
<213> ORGANISM: Artificial
<220> FEATURE:
<223> OTHER INFORMATION: primer P15

<400> SEQUENCE: 21
gtactagaat tcgtgtaatt gcggagactt tgcg                                 34

<210> SEQ ID NO 22
<211> LENGTH: 41
<212> TYPE: DNA
<213> ORGANISM: Artificial
<220> FEATURE:
<223> OTHER INFORMATION: primer P16

<400> SEQUENCE: 22
aatagcctgc agttatttga tttcaattt gtcccactcc c                          41

<210> SEQ ID NO 23
<211> LENGTH: 60
<212> TYPE: DNA
<213> ORGANISM: Artificial
<220> FEATURE:

```
<223> OTHER INFORMATION: primer P17

<400> SEQUENCE: 23
tcagctgtta aaaggggatg tgttatccag caccgctgaa gcctgctttt ttatactaag      60

<210> SEQ ID NO 24
<211> LENGTH: 59
<212> TYPE: DNA
<213> ORGANISM: Artificial
<220> FEATURE:
<223> OTHER INFORMATION: primer P18

<400> SEQUENCE: 24
atgagcgtaa aagttatcgt cacagacatg gacggcgctc aagttagtat aaaaaagct      59

<210> SEQ ID NO 25
<211> LENGTH: 18
<212> TYPE: DNA
<213> ORGANISM: Artificial
<220> FEATURE:
<223> OTHER INFORMATION: primer P19

<400> SEQUENCE: 25
atttgtgctc tgcgtcac                                                   18

<210> SEQ ID NO 26
<211> LENGTH: 20
<212> TYPE: DNA
<213> ORGANISM: Artificial
<220> FEATURE:
<223> OTHER INFORMATION: primer P20

<400> SEQUENCE: 26
ttgatgtgat gtacaggatg                                                 20

<210> SEQ ID NO 27
<211> LENGTH: 19
<212> TYPE: DNA
<213> ORGANISM: Artificial
<220> FEATURE:
<223> OTHER INFORMATION: primer P21

<400> SEQUENCE: 27
agctacctct ctctgattc                                                  19

<210> SEQ ID NO 28
<211> LENGTH: 19
<212> TYPE: DNA
<213> ORGANISM: Artificial
<220> FEATURE:
<223> OTHER INFORMATION: primer P22

<400> SEQUENCE: 28
tgtttcccat agcatcctc                                                  19
```